United States Patent [19]

Yamashita et al.

[11] Patent Number: 5,332,668
[45] Date of Patent: Jul. 26, 1994

[54] **PROTEASE WITH LOW THERMOSTABILITY DERIVED FROM *MUCOR PUSILLUS***

[75] Inventors: Takashi Yamashita, Hachioji; Susumu Higashi, Higashi Murayama; Toshihiko Higashi, Hachioji; Haruo Machida; Shinjiro Iwasaki, both of Hino; Teruhiko Beppu, Tokyo, all of Japan

[73] Assignee: Meito Sangyo Co., Ltd., Aichi, Japan

[21] Appl. No.: 958,222

[22] Filed: Oct. 8, 1992

[30] Foreign Application Priority Data

Oct. 11, 1991 [JP] Japan .................. 3-263878

[51] Int. Cl.⁵ .......................... C12N 9/50; C12N 9/58
[52] U.S. Cl. ..................................... 435/223; 435/219; 435/931
[58] Field of Search .................. 435/223, 931; 530/823

[56] References Cited

FOREIGN PATENT DOCUMENTS

| | | |
|---|---|---|
| 0230231 | 1/1987 | European Pat. Off. . |
| 0443476 | 2/1991 | European Pat. Off. . |
| 218834 | 10/1983 | Japan . |
| 62-40999 | 9/1984 | Japan . |
| 61-185186 | 8/1986 | Japan . |

OTHER PUBLICATIONS

Hiramatsu, R. et al.; J. Biol. Chem. 264: 16862–16866 (1989).
Branner, S. et al.; Ann. N.Y. Acad. Sciences, vol. 434, pp. 340–342.
Darnell, J. et al.; Molecular Cell Biology, Scientific American Books, N.Y. (1984), pp. 53–55.
Brock, T. D..et al.; Biology of Microorganisms, Fourth Ed., Prentice-Hall Inc., N.J. (1984), pp. 302–312.
Beppu, T., Database WPIL, Week 8801 (1987).
Beppu, et al., *Modification of milk–clotting aspartic proteases, chymosin and Mucor rennin* Chemical Abstracts, vol. 113, No. 23, 207369z Columbus, Ohio.
Aikawa, et al., *Advances in Experimental Medicine and Biology*, vol. 306, 1991, New York US, pp. 233–242.
Branner-Jorgensen, et al.; Neth. Milk Dairy J. 35 (1981) 361–364; "Reduced thermostability of modified *Mucor miehei* rennet".
Suzuki, et al.; Portein Engineering vol. 2, No. 7, pp. 563–569, 1989; "Alteration of catalytic properties of chymosin by site-directed mutagenesis".

*Primary Examiner*—Robert A. Wax
*Assistant Examiner*—Eric Grimes
*Attorney, Agent, or Firm*—Knobbe Martens Olson & Bear

[57] ABSTRACT

A mutant fungus strain which produces a protease with low thermostability and low productivity was made from protease producing fungi and the gene coding for mutant enzyme is isolated from the mutant strain. A promoter which can function in yeast is ligated to the gene and inserted into a plasmid replicable in yeast, and the resulting plasmid is introduced into yeast. The yeast is cultured, thereby producing the mutant enzyme. Furthermore, a gene expressing an enzyme with a far lower thermostability is prepared by site-directed mutagenesis, which is introduced in yeast, thereby producing an enzyme with more distinctively reduced thermostability.

3 Claims, 12 Drawing Sheets

PROTEASE WITH LOW THERMOSTABILITY DERIVED FROM *MUCOR PUSILLUS*

BACKGROUND OF THE INVENTION

The present invention relates to proteases with low thermostability, genes required for producing the same and plasmids containing the gene, microorganisms carrying the plasmid, and a method for producing the protease using these microorganism. More specifically, this invention relates to a milk clotting enzyme for use in cheese production.

As the protease for cheese production, i.e., a milk clotting enzyme, calf rennet has conventionally been employed. The milk clotting activity of calf rennet is predominantly attributable to chymosin as an acid protease, and it is because of the higher specificity to milk casein and the low thermostability that chymosin is an excellent milk clotting enzyme.

With the decrease in the number of slaughtered calves, however, the stable supply of calf rennet has also been decreasing. As an alternative enzyme to calf rennet,"microbial rennets", representatively illustrated by Mucor rennet (MR) produced by *Mucor pusillus* (Japanese Patent Publication No. 40-18830) are therefore predominantly used as rennet.

However, many of these enzymes have a low ratio of C/P (a ratio of milk clotting activity to proteolitic activity) which is important as a milk clotting enzyme property. The result is that some of these enzymes deteriorate cheese flavor. Also, many of the enzymes generate bitter peptides during ripening because the enzymes have a relatively high thermostability, and are not inactivated during the cooking process in cheese production.

In order to solve these problems, the production of calf chymosin by introducing the gene thereof into *Escherichia coli* (*E. coli*) and the like was accomplished by using genetic engineering techniques (Japanese Patent Publication No. 62-40999).

Attempts have also been made to lower the thermostability of MR, which is the preferred microbial rennet, by chemical modification of the enzyme (Japanese Patent Publication No. 2-18834; Japanese Patent Laid-Open Publication No. 61-185186 and vice versa).

Although these methods have been somewhat successful, they are not satisfactory. Thus, a type of enzyme with a higher C/P ratio and a lower thermostability has been demanded.

Alternatively, the cloning of the MR gene has been established (Tonouchi, N., et al., *Nucleic Acid Res.* 14, 7557–7568(1986)), and the present inventors disclose that the gene can be expressed in yeast (Yamashita, T., et al., *Mol. Gen. Genet.* 210, 462–467 (1987)).

However, all of the plasmids used for the expression of the MR gene in yeast delete a part of the LEU2 gene, so the transformation efficiency thereof in yeast is not high. Also, such plasmids are inconvenient for handling. For example, it is hard to manipulate the plasmids, because the plasmids each have an unnecessary sequence downstream from the terminator and have the sequence of a whole length of 2 $\mu$m DNA. In addition, these plasmids are unstable.

Therefore, a means of using yeast to stably supply milk clotting enzymes having a higher C/P ratio and a lower thermostability is desired.

SUMMARY OF THE INVENTION

The present invention provides a protease with low thermostability, the gene required for producing the same and plasmids containing the gene, microorganisms carrying the plasmid, and a method for producing the protease using these microorganisms.

The present invention will now be explained in detail.

1. Protease with low thermostability

In accordance with the present invention, the protease with low thermostability is a protease having an amino acid sequence represented by amino acid numbers from 1 to 361 in the SEQ ID NO:2, wherein the amino acid 101 is substituted by threonine or the amino acid 186 is additionally substituted by an amino acid other than glycine, or having an amino acid sequence represented by amino acid numbers from 1 to 361 in SEQ ID NO:2, wherein the amino acid 186 is substituted by an amino acid other than glycine.

The protease with low thermostability in accordance with the present invention can be generated by preparing a mutant strain of microorganism which produces a protease with low thermostability from a microorganism producing a protease with a relatively high thermostability, isolating the gene of a mutant protease from the mutant strain and integrating the gene into a vector or isolating the gene of a wild protease from the original strain, integrating a modified gene through the combination of these genes into a vector and introducing the resulting plasmid into a microorganism and cultivating the resulting transformant.

A protease different from the protease described above can be obtained by further modifying the modified gene by site-directed mutagenesis.

These procedures are now described hereinbelow.

1.1 Preparation of a mutant strain generating a protease with low thermostability A mutant strain generating a type of enzyme with low thermostability can be prepared through artificial mutagenesis. As the original strain used for preparing a mutant strain, any microorganism may be used which can produce a protease applicable as a milk clotting enzyme, but preference is given to those producing an extracellular protease due to the easy purification thereof.

Such microorganisms include *Mucor pusillus*, *Mucor miehei*, *Endothia parasitica* and the like. Preference is given to *Mucor pusillus*.

No limitation is imposed on the process of such mutagenesis. Generally employed methods for mutation can be employed, including a physical process such as UV irradiation, or a process with a mutagen such as ethyl methanesulfonate (EMS), N-methyl-N'-nitro-N-nitrosoguanidine (NTG) and the like.

An example of the preparation of a mutant strain based on *Mucor pusillus* is now explained hereinbelow.

*Mucor pusillus* is cultured on a koji plate at 37° C. to form spores. The spores are suspended in sterile water using a glass spreader, followed by addition of N-methyl-N'-nitro-N-nitrosoguanidine prior to treatment at ambient temperature for 5 to 20 minutes to a final death rate of 90%. An appropriate amount of the resulting suspension is spread on a koji plate for culturing at 37° C.

1.2 Selection of a mutant strain

The selection of a mutant strain producing an enzyme with low thermostability can be carried out by subjecting the culture broth of the mutagenized microorganism to thermal treatment as it is or after it is concentrated, and comparing the milk clotting activity prior to thermal treatment with the activity after such treatment.

An example of the method for measuring the milk clotting activity is a method comprising adding 0.01 ml of a sample to 1 ml of 10% skim milk dissolved in a 10 mM aqueous calcium chloride solution, and keeping the mixture at 37° C., and measuring the time period required for milk clotting. As the milk clotting activity is proportional to the reciprocal time period required for solidification, the ratio of the remaining activity can be determined by comparing the time required for solidification, the ratio of the remaining activity can be determined by comparing the time required for milk clotting in a sample prior to heating with the time after heating. Thus, thermostability can be compared between enzymes.

For example, a three-fold volume of cold ethanol is added to the culture supernatant of the mutagenized *Mucor pusillus* to precipitate protein, and the precipitate is dissolved in a buffer of 50 mM sodium acetate, pH 6.0, containing 5 mM EDTA. A part of the solution is taken out and subjected to heating at 55° C. for 20 minutes, then immediately cooled to ambient temperature.

The sample (0.01 ml) is added to 1 ml of 10% skim milk (manufactured by DIFCO Laboratories, U.S.A.) dissolved in an aqueous 10 mM calcium chloride solution, which is then kept at 37° C. By measuring the time period required for milk clotting prior to and after the thermal treatment, the ratio of the remaining activity after the thermal treatment is determined. By using this procedure, a mutant strain producing a mutant enzyme with thermostability far lower than the thermostability of the MR produced by the original strain may be selected.

The protease with low thermostability in accordance with the present invention can be obtained by isolating a mutant protease gene from the mutant strain selected in the manner described above, and expressing the gene or a further modified gene in other microorganisms. Specific procedures for isolating mutant genes, preparing plasmids and the like are explained below.

2. Gene coding for the protease with low thermostability 2.1 Isolation of a mutant gene If a protease with lowered thermostability can be generated efficiently through mutagenesis, the mutant strain may be used for protease generation. In many cases, however, mutation is also incurred in those other than the target gene by the mutagenesis, resulting in the reduction of the productivity.

In such cases, it is preferred that the yield should be increased by isolating the protease gene and subjecting the gene to genetic recombination techniques. Only if the gene is isolated, another mutation can be introduced following protein engineering technique. Routine gene cloning methods may be used to isolate the gene, comprising, for example, purifying an enzyme, determining the amino acid sequence, preparing a synthetic oligonucleotide probe on the basis of the amino acid sequence and selecting a gene from a gene library by hybridization.

Methods for DNA cleavage, ligation and transformation are described in a manual attached to commercially available enzyme and competent cell products to be used for individual procedures.

The methods essential for general genetic recombination, including these procedures, the determination of the nucleotide sequence of a gene, and the hybridization thereof are described in *Molecular Cloning*, Maniatis et al., Cold Spring Harbor Laboratory Press.

Because the cloning of the MR gene is already established, a protease gene with low thermostability can be yielded from a *Mucor pusillus* mutant strain which is prepared by the above procedures and generates a protease with low thermostability, by splicing out MR gene from MR gene-containing plasmid JP1 (*Mol. Gent. Gent.* 210, 462–467(1987)) and carrying out plaque hybridization, etc. employing the gene as a probe.

If a gene having a part of an original gene or a plurality of genes each having different mutation sites are obtained, a different mutant gene can also be prepared by ligating the mutant genes or by ligating one of the mutant genes with a wild gene.

2.2 Introduction of a site-directed mutagenesis

It is expected that if a rennet gene is isolated, mutation can be introduced in a more intended manner, thereby preparing an enzyme gene with lower thermostability. An enzyme with a variation in the C/P ratio can be obtained expectably.

A mutation can be introduced, for example, by synthesizing a sequence having a restriction enzyme recognition sequence at both of the termini thereof and further containing the sequence having base exchange around a mutation point, and substituting the sequence with a corresponding sequence of wild gene (cassette mutagenesis). If an appropriate restriction enzyme site is not available near the mutation site, this method is, in many cases, difficult.

On the contrary, site-directed mutagenesis is more preferable because a mutation can be introduced whether a restriction site is present or not. The gapped duplex method and the Kunkel method are illustrated as the method for introducing such site-directed mutagenesis. The Kunkel method principally comprises cloning a wild gene into a single-stranded phage, using a synthetic DNA containing a mismatch at the mutation site as a primer to synthesize a chain complementary to the primer, and preparing a new phage and a replicative-form DNA employing only the complementary chain containing the obtained mutation as a template.

For site-directed mutagenesis, a commercially available kit can be used. The selection of the mutant gene can be accomplished by determining the milk clotting activity of the culture broth of the microorganisms harbouring such genes.

3. Plasmid containing the gene coding for the protease with low thermostability

The gene thus obtained as described above is introduced into an appropriate host-vector system. As such a host, *E. coli, Bacillus*, yeast, filamentous fungus, cultured cell, etc. may be illustrated, and preference is given to yeast in terms of stability of the vector, expression while retaining the activity, and the possibility of extracellular production (protein secretion).

Such yeast may be illustrated by the strains of *Saccharomyces cerevisiae*, i.e., SHY3, D13-1A, and MC16. These strains have auxotrophic mutation, so a vector can be prepared by integrating a gene complementing those mutations into a plasmid replicable in yeast.

For example, the MC16 strain requires leucine for growth. When a gene complementing the leucine requirement is carried on a plasmid and transferred into yeast, those which do not require leucine for growth are generally considered as such carrying the plasmid.

As the plasmid replicable in yeast, any type of so-called YIp, YRp, YEp, and YCp may be used, but YEp type is preferable from the viewpoints of copy number and stability. Because these plasmids generally contain unnecessary sequences, the plasmids are preferably used after the unnecessary sequences are removed in order to stabilize the plasmids or in order to readily modify the plasmids.

A preferable vector is illustrated, for example, by plasmid JS3 (which is described in details in the embodiments) prepared by using YEp13 (J. R. Broach et al., Gene 9, 287 (1980)) as a starting plasmid.

Following the selection and preparation of an appropriate host-vector system, the linking of an appropriate promoter and a terminator, if necessary, to the mutant gene is required. Nevertheless, it is not the case when the promoter of the original strain functions with efficiency in the host.

As such a promoter, trp, lac, tac, $\lambda P_L$, etc. may be used, provided that the host is E. coli. When yeast is used for the host, GAL7, ADH, TPI, PHO5, etc. may be used and among them, preference is given particularly to GAL7 (Nogi Y., et al., Nucl. Acids Res. 11, 8555–8568(1983)) because it is potent and inducible.

As such a terminator, TPI, GAPDH, GAL10, etc. may be included.

A product obtained by ligating the promoter, the protease gene with low thermostability of the present invention, and the terminator described above in this sequential order can be inserted into the vector, whereby the plasmid of the present invention can be prepared.

An embodiment of preparing a plasmid will be shown below, employing Saccharomyces cerevisiae as such host and JS3 as a vector.

4. Saccharomyces cerevisiae carrying the plasmid of the present invention

By introducing the plasmid prepared as described above into a microorganism, a microorganism producing the protease with low thermostability can be prepared. An example of the transformation of Saccharomyces cerevisiae is described hereinbelow.

Saccharomyces cerevisiae, which has preliminarily been cultured overnight in a YPD medium (1% yeast extract manufactured by DIFCO Laboratories, U.S.A., 2% Bacto peptone, manufactured by DIFCO Laboratories, U.S.A., and 2% glucose) is inoculated at 10% (V/V) in a fresh YPD medium and cultured at 30° C. for 4 hours. The culture broth (1.5 ml) is mildly centrifuged with a bench-top centrifuge to collect cells, and followed by rinsing in 0.2M LiSCN (manufactured by Kanto Chemical Co., Ltd.). The cells are then suspended in 0.02 ml of 1M LiSCN.

The plasmid solution (0.01 ml; about 1 to 10 μg) is mixed well with 0.03 ml of 70% PEG 4000, and kept at 30° C. for 1 hour. To the resulting solution is added 0.14 ml of sterile water for dilution, this is then plated on two SDah plates (0.67% Bacto-yeast nitrogen base w/o amino acid, 2% glucose, 0.002% adenine sulfate, 0.002% L-histidine-HCl, and 2% agar). The plates are incubated at 30° C. for 2 to 3 days, thereby yielding transformants.

The transformants obtained by transforming a Saccharomyces cerevisiae MC16 strain with the plasmids JS52, JS53, and JS525 explained in the embodiments described below are deposited as Accession Numbers FERM BP3898, BP3900 and BP3899, respectively, with the Patent Microorganism Depository, Fermentation Research Institute, Agency of Industrial Science and Technology at 1-3, Higashi 1-chome, Tsukuba-shi, Ibarakiken, 305, Japan.

5. Method for producing a protease with low thermal resistance

By cultivation of the transformants carrying the plasmids, proteases with low thermostability can be produced. For the cultivation of the microorganism, induction is preferably performed if an inducible promoter is used. An example of the method for culturing a transformant of Saccharomyces cerevisiae is explained hereinbelow.

The transformant is subjected to shake culture at 30° C. in 50 ml of the YPD medium placed in a 500-ml Sakaguchi flask for 2 days, to proliferate the cells. The culture broth is centrifuged at 1,000×g for 5 minutes, to collect the cells, which are resuspended in 100 ml of a YPGal medium (1% yeast extract, 2% Bacto peptone, 4% galactose (manufactured by WAKO Chemicals Co., Ltd.)). The suspension is subjected to shake culture in a 500-ml Sakaguchi flask at 30° C. for 3 days.

The mutant enzyme prepared is purified by employing routine protein purification methods, namely ion exchange or gel filtration chromatography, salting out with ammonium sulfate, precipitation with organic solvents, and the like. The purification of MR is now illustrated hereinbelow.

The culture broth is centrifuged at 1,000×g for 10 minutes, and the resulting supernatant of 200 ml is diluted two-fold with 20 mM sodium acetate buffer, pH 6.0, containing 5 mM EDTA, which is then passed through 30 ml of an ion exchanger, DEAE-TOYOPEARL 650M (manufactured by TOSOH Co., Ltd.), equilibrated with the same buffer. The MR protein secreted outside the cell is adsorbed onto the exchanger along with a part of the pigment in the supernatant of the culture broth, and subsequently eluted with the same buffer supplemented with 0.4M NaCl.

The purified enzyme may be concentrated by lyophilization, ultrafiltration, precipitation with an organic solvent and the like.

BRIEF DESCRIPTION OF THE DRAWINGS

The following legend depicts the symbols representing the functions of DNA sequences used in FIGS. 1–12.

LEGEND for FIGURES 1–12

■ MR contsing 3' and 5' portions
▨ non-identified Mucor DNA
▨ GAL7 promoter
▨ GAL10 terminator
▨ region GAL7 or GAL10 gene
☰ LEUS2 or leus2-d
▤ 3' or 5' portion of LEU2
▨ 2 μm region including a replication origin
▨ other 2 μm regions

DESCRIPTION OF PREFERRED EMBODIMENTS

Figure 1:
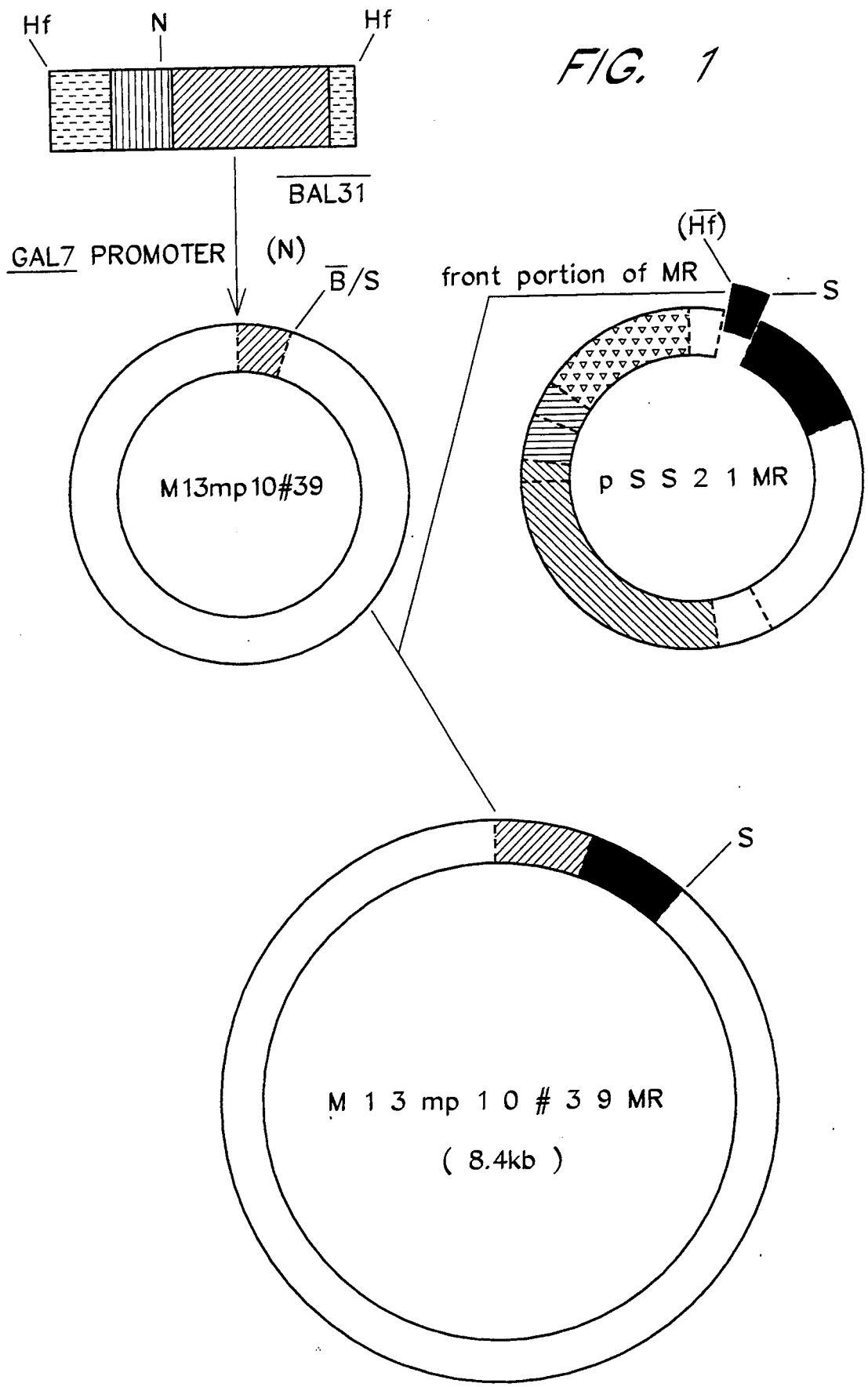
FIG. 1 depicts the process of preparing plasmid M13mp10#39MR.

The present invention will now be explained with reference to embodiments.

Gene:

The symbols representing the functions of DNA sequences used in the figures depicting the plasmid preparation process are shown in the foregoing legend and as follows:

Blanks: represent vectors including pBR322, pAT153, M13mp10 and the like.

Parentheses: indicate the deletion of restriction enzyme recognition sites after ligation.

Overline: indicates a repaired terminus.

Blank asterisk symbol: indicates the mutation of amino acid 101.

Black asterisk symbol: indicates the mutation of amino acid 186.

The abbreviated symbols of restriction enzymes used in the figures are as follows:

| Ac:  | AccI           | Hp:  | HpaI     |
|------|----------------|------|----------|
| Alu: | AluI           | N:   | NcoI     |
| B:   | BamHI          | P:   | PstI     |
| Bst: | BstPI (= BstEII) | S:   | SalI     |
| E:   | EcoRI          | Sc:  | SacI     |
| G:   | BglII          | Sp:  | SphI     |
| Hc:  | HincII         | Ssp: | SspI     |
| Hf:  | HinfI          | Tth: | TthIII-I |

General procedures used in the individual steps of the present embodiments, such as the step of plasmid construction, are shown as follows.

(Restriction enzyme reaction)

Unless otherwise stated, the restriction enzyme reaction was carried out by using the following composition;

DNA: 0.1 to 5.0 μg;

buffer for universal use (10×): 10 μl;

restriction enzyme (manufactured by TAKARA SHUZO Co., Ltd.): 2 to 12 units;

volume of reaction solution: 100 μl.

The buffer for universal use is a buffer, pH 7.5 to 8.5, containing 5 to 10 mM dithiothreitol, 100 to 500 mM Tris-HCl or Tris-acetate, 100 mM magnesium chloride or magnesium acetate, and an appropriate concentration of sodium chloride, potassium chloride or potassium acetate.

After subjecting the reaction solution to 1 hour at 37° C. in an incubator, phenol extraction and ethanol precipitation were performed to dissolve the resulting solution in an appropriate amount of TE (10 mM Tris-HCl, pH 7.5, 1 mM EDTA). By the term "phenol extraction" is meant herein a procedure comprising adding an equal volume of TE saturated phenol (phenol manufactured by WAKO Chemical Co., Ltd.) prior to sufficient stirring, followed by centrifuge, thereby recovering the aqueous phase, adding phenol-chloroform (TE saturated phenol:chloroform:isoamyl alcohol=50:49:1) at an amount equal to the volume of the recovered phase, followed by stirring and centrifuge, thereafter recovering the aqueous phase, and extracting and removing the phenol remaining in the aqueous phase using diethyl ether. By the term "ethanol precipitation" is meant a procedure comprising adding a 1/10 volume of 3M sodium acetate and a 2.5-fold volume of ethanol to a DNA solution prior to agitation, cooling the solution at −80° C. for 10 minutes and centrifuging to remove the supernatant, and recovering the precipitate, and if necessary, drying the precipitate under reduced pressure and dissolving in an appropriate solvent.

(Blunting DNA termini)

Cohesive ends produced by cleavage of DNA with restriction enzymes were blunt ended by using a DNA blunting kit, manufactured by TAKARA SHUZO Co., Ltd., and utilizing the 5' to 3' polymerase activity and 3' to 5' exonuclease activity of T4 DNA polymerase.

(Electrophoresis)

Using 40 mM Tris-acetate buffer containing 2 mM EDTA and additionally using an electrophoretic bath, Mupid-2 (manufactured by Cosmo Bio Co., Ltd.), electrophoresis was done at a constant voltage of 100 V or 50 V. As the agarose gel for electrophoresis, Seakem ME or GTG (purchased from TAKARA SHUZO Co., Ltd.) was used at a concentration of 0.8 to 4%, depending on the size of fragments to be separated.

(Purification of DNA fragments)

Using a DNA purifying kit, GENECLEAN II (manufactured by BIO 101 Co., Ltd.), the agarose containing a DNA fragment was solubilized in a potassium iodide solution, and then the DNA was adsorbed onto glass powder and eluted with a buffer of low salt concentration.

(DNA ligation)

The DNA fragment cleaved with a restriction enzyme, or the fragment further blunt ended if necessary, was ligated using a DNA ligation kit using T4 DNA ligase (manufactured by TAKARA SHUZO Co., Ltd.). Specifically, if three fragments were ligated together, the content of a vector was reduced about ⅓ fold, thereby improving the ligation efficiency.

1. Generation of a mutant strain producing a type of a milk clotting enzyme with low thermostability A strain of *Mucor pusillus* IFO4578(+) which produces MR was subjected to the mutation process, to obtain a mutant strain secreting an MR with lowered thermostability. Detailed explanation will now follow.

1.1 Mutation process

The strain *Mucor pusillus* IFO4578(+) was grown on a koji plate (koji extract purchased from Koji-ya Sanzaemon: diluted to a sugar level to 9%, and then adjusted to pH 6.0, using sodium hydroxide, 2% agar) and kept at 37° C. for 3 to 7 days, whereby spores were formed. These spores were suspended in sterile water using a glass spreader.

To the spore suspension was added N-methyl-N'-nitro-N-nitrosoguanidine (manufactured by SIGMA CHEMICAL Co.) to give a final concentration of 200 μg/ml, and treated at ambient temperature for 5 to 20 minutes to a death rate of 90%. An appropriate amount thereof was then spread on a koji plate, and kept at 37° C. Each mass of the microhyphae was inoculated on 2 ml of the koji medium placed in a test tube of 13 mm Φ and cultivated with shaking at 37° C. for 4 days. The resulting supernatant was designated as a sample for measuring milk clotting activity (referred to as MCA hereinafter). The mycelium were stored at −80° C.

1.2 Screening of a mutant strain

A three-fold volume of cold ethanol was added to the culture supernatant to precipitate protein, and the precipitate was dissolved in 50 mm sodium acetate buffer, pH 6.0, containing 5 mM EDTA. A part of the solution was taken out and heated at 55° C. for 20 minutes, immediately followed by cooling to ambient temperature. The sample (0.01 ml) was added to 1 ml of 10% skim milk (manufactured by DIFCO Laboratories, U.S.A.) dissolved in an aqueous 10 mM calcium chloride solution and kept at 37° C. The time required for milk clotting was measured, prior to and after the thermal treatment, thereby determining the remaining activity ratio after the thermal treatment. In such manner, a mutant strain was selected, which generated a mutant enzyme with thermostability far lower than the thermostability of the MR produced by the original strain IFO4578(+). As a result, a mutant strain with much less thermostability than that of the IFO4578(+) strain was obtained and designated as 301-7 strain.

2. Isolation of mutant MR gene 2.1 Preparation of chromosomal DNA of a mutant strain The mutant strain 301-7 obtained above was grown on a koji plate and kept at 37° C. for 3 to 7 days, whereby spores were formed. The spores were suspended in sterile water using a glass spreader. To about $10^8$ per flask, the spore suspension was inoculated in 100 ml of the YPG liquid medium in each of ten 500-ml Sakaguchi flasks, and cultured at 37° C. for 4 days. As the mycelium formed a pellet of a size of about 0.5 mm to 2 mm, the culture broth was filtered, thereby removing excess water, to obtain the mycelium of a wet weight of 26.7 g.

After being frozen in liquid nitrogen, the mycelium were prepared into powder under cooling in liquid nitrogen, using a homogenizer, type AM-7, manufactured by Nihon Seiki Seisaku-sho Co., Ltd.

The resulting powder was suspended in 100 ml of 0.5M EDTA, pH 8.0 and 0.5% SDS, supplemented with proteinase K (purchased from Nippon Gene Co., Ltd.), and the resulting suspension was then kept at 55° C. overnight. The suspension was filtered through two-layered gauze, followed by the addition of an equal volume of phenol prior to agitation, and then subjected at least twice to the process for recovering the aqueous phase. The aqueous phase was diluted with an equal volume of TE (10 mM Tris-HCl, pH 8.0, 1 mM EDTA), followed by addition of 1/10 volume of 3M sodium acetate and a ½ volume of ethanol to precipitate nucleic acids, and the precipitate was dissolved in 1 ml of TE. Purification was performed if necessary, by cesium chloride equilibrium density gradient centrifugation.

2.2 Preparation of a chromosomal DNA library

About 10 μg of the genomic DNA of the 301-7 strain was partially digested with 2 units of restriction enzyme Sau3AI. One, two, four and 11 minutes after the initiation of the reaction, sampling was performed. A part of each of the samples was subjected to electrophoresis on agarose gel, to select a reaction solution containing a great number of fragments of a length of 10 kb or more. The selected solution was processed by phenol extraction and ethanol precipitation, and the resulting precipitate was dissolved in 4 μl of TE.

As the vector for the libraries, 1 μl of λEMBL3 BamHI Arms (purchased from Promega Co., Ltd.) or λDASH BamHI (purchased from STRATAGENE Co., Ltd.) was used, to which were ligated the DNA fragments obtained above, using a ligation kit (manufactured by TAKARA SHUZO Co., Ltd.). The resulting ligated vector was subjected to in vitro packaging, using an in vitro packaging kit (manufactured by Amersham Japan Co., Ltd.) or Gigapack packaging kit (STRATAGENE Co., Ltd.), which was then overlaid along with an indicator bacterium E. coli LE392 on an agar medium to generate a phage plaque.

Two libraries were constructed, and plaques of 2,000 to 7,000 were obtained in both libraries.

2.3 Isolation of a mutant MR gene

The plasmid JP1 which contains wild MR gene (Mol. Gen. Genet. 210, 462–467(1987)) (described below) was digested with restriction enzymes BamHI and BglII, to recover 1.4-kb fragments. Using Multiprime DNA labeling systems manufactured by Amersham Japan Co., Ltd., 25 ng of the fragments were labeled with $^{32}P$ by random primer method, and the labeled product was designated as the probe for plaque hybridization.

Using the probe, the plaque hybridization of the libraries was done.

The plaque of the recombinant phage was transferred onto a nylon membrane Colony/PlaqueScreen (manufactured by NEN Research Products Co., Ltd.) and treated with 0.5N NaOH and 1.0M Tris-HCl, pH 7.5, following the supplier's direction, to fix the DNA onto the membrane. According to the method recommended on the protocol, prehybridization and hybridization were done at 65° C., followed by washing and drying prior to exposure to an X-ray film to image an autoradiogram. Based on the positive signal on the film, plaques hybridized with the probes were identified.

One and three positive plaques were obtained from the first and second library, respectively.

The phage of the positive plaques was suspended in 0.5 ml of SM (50 mM Tris-HCl, pH 7.5, 0.58% NaCl, 0.2% $MgSO_4.7H_2O$, 0.01% gelatin (manufactured by DIFCO Laboratories, U.S.A.)), which was defined as a phage suspension. Along with E. coli LE392 as an indicator bacterium, the suspension was layered on an LB plate supplemented with 10 mM $MgSO_4$. After plaques were formed, the layered agar was scrubbed, which was subsequently suspended in the SM to obtain a concentrated phage suspension.

The concentrated phage suspension (0.04 ml) and 0.08 ml of the culture broth of the E. coli LE392 cultured overnight were added to 100 ml of an LB medium supplemented with 10 mM $MgSO_4$ in a 500-ml Sakaguchi flask, which was then shake-cultured at 37° C. for 6 hours. After the lysis of the indicator bacteria with the phage was confirmed, chloroform (1 ml) and sodium chloride of a final concentration of 1M were added, followed by shaking for another 10 minutes for complete lysis.

The lytic solution was centrifuged at 8,000×g for 10 minutes, thereby recovering the supernatant, followed by the addition of 10 g of PEG 6,000 (manufactured by WAKO Chemicals Co., Ltd.), which was then let to stand at 4° C. overnight and centrifuged at 8,000×g for 10 minutes. The resulting precipitate was dissolved in 1 ml of the SM. Then, RNase A and DNase I were added to final concentrations of 1 μg/ml and 10 μg/ml, respectively, and then kept at 37° C. for 30 minutes. Cesium chloride was added and dissolved in the solution at 0.5 g per ml, and the resulting solution was laid on a discontinuous density gradient in a centrifuge tube, comprising multi-layers of 1 ml, 3 ml and 2 ml of individual solutions of cesium chloride (WAKO Chemicals Co., Ltd.) preliminarily adjusted to densities 1.6, 1.5 and 1.4 g/cm$^3$, respectively.

The tube was centrifuged at 200,000×g at 20° C. for 6 hours, thereby recovering the phage particles accumulating at the interface of the cesium chloride solutions of the densities of 1.4 and 1.5 g/cm$^3$. A part of the suspension of the phage particles was diluted with TE, followed by phenol extraction and ethanol precipitation, and the resulting precipitate was then dissolved in 400 μl of TE. Thus, the phage DNA was obtained.

Subsequently, the fragments containing the MR gene were analyzed by Southern blotting.

The phage DNA (5 μg) obtained above was digested with restriction enzymes, PvuII, EcoRI, and HindIII, separately, followed by phenol extraction and ethanol precipitation, and then subjected to electrophoresis on 1% agarose gel.

After electrophoresis, the gel was immersed with gentle shaking in 0.25M HCl for 20 minutes, then twice in a solution of 0.6M NaCl and 0.4N NaOH for 15 minutes each, and then in a solution of 1.5M NaCl and 0.5M Tris-HCl (pH 7.5) for 20 minutes.

Then, the gel was placed on a filter paper immersed in 10×SSC (1.5M NaCl-0.15M sodium citrate solution), on which was laid a nylon membrane GeneScreen Plus (manufactured by NEN Research Products Co., Ltd.). An edge of the filter paper was immersed in 10×SSC, so that the 10×SSC could be soaked up. Furthermore, paper towel was laid on the membrane in order that the 10×SSC might be soaked up through the membrane from the filter.

After allowing to stand overnight, the membrane was simply washed in purified water, and air dried. Under the same conditions as for the plaque hybridization, the probe was hybridized and the membrane was subjected to autoradiography. Subsequently, it was confirmed which fragment carried the MR gene among the fragments cleaved with the individual restriction enzymes.

As a result, it was found that the phage obtained from the first library carried the MR gene on a 3.5-kb EcoRI fragment, so that the fragment of 0.5 μg was recovered from the gel after electrophoresis.

Alternatively, plasmid pUC18 (purchased from TAKARA SHUZO Co., Ltd.) (0.2 μg) was cleaved with the restriction enzyme EcoRI, followed by addition of a two-fold volume of 1M Tris-HCl, pH 8.0, and 0.3 unit of *E. coli* alkaline phosphatase (purchased from TAKARA SHUZO Co., Ltd.) and then kept at 37° C. for one hour to dephosphorylate the cleavaged terminus. After further phenol extraction and ethanol precipitation, the resulting plasmid was dissolved in 5 μl of TE. *E. coli* JM109 was transformed with the plasmid ligated with the EcoRI fragment yielding a plasmid p31E.

The DNA of one (λ1) of the three phages obtained from the second library was Southern hybridized, and the result indicates that the phage had a restriction map different from that of p31E. Thus, the 2-kb SalI-HindIII fragment and 1-kb PvuII-ClaI fragment, both having MR gene, were separately spliced out and then ligated into pBluescriptII SK+ (manufactured by STRATAGENE Co., Ltd.) digested with restriction enzymes SalI and HindIII, or with PvuII and ClaI. These were designated as plasmids pλ1SH and pλ1PvC, respectively.

Using a nucleotide sequence determination kit, 7-deaza Sequenase Ver. 2 for labeled dCTP kit (purchased from TOYOBO Co., Ltd.) and following the supplier's instruction, dideoxy chain termination method was used to determine the nucleotide sequence of the MR gene derived from the mutant strains thus obtained. Following the same method, the nucleotide sequence of the proximity of a mutation point introduced with a site-directed mutagenesis described later was also confirmed.

A single stranded DNA to be used for the determination of the nucleotide sequence was obtained as follows. The plasmids p31E, pλ1SH, and pλ1PvC were digested with restriction enzymes EcoRI, HindIII, ClaI, HincII, BglII, SalI, BamHI, AccI and the like, singly or doubly, and the resulting fragments were subcloned into phage M13mp18 or M13mp19 RF (replicative form) DNA (purchased from TAKARA SHUZO Co., Ltd.) digested with one or two restriction enzymes which can produce termini complementary to the fragments. According to the supplier's instruction, the culture supernatant of *E. coli* containing the individual phages was subjected to precipitation with PEG (polyethylene glycol) 6,000 and phenol extraction, thereby generating a single stranded phage DNA.

Using the single stranded phage DNA, the analysis of the nucleotide sequence was performed. As a result, the codon of the amino acid 101 numbered from the N terminus in the MR gene of p31E was not the codon of alanine (GCT) in the wild enzyme but the codon of threonine (ACT). The MR gene of p31E did not contain the region encoding the amino acids 223 and thereafter (downstream from base number 1224 in SEQ ID NO:2). The codon of the amino acid 186 in the MR gene of λ1 was not the codon of glycine in the wild enzyme, but the codon of aspartic acid (GAC). The region encoding the amino acids up to position 5 (upstream from base number 571) was deleted in the MR gene of λ1.

The nucleotide sequence and amino acid sequence shown in the Sequence Listing (SEQ ID NO:1 and SEQ ID NO:2, respectively) are the sequences of the wild MR gene. It is known that MR is generated as a preproprotein; the signal peptide composed of 18 amino acids is cleaved to generate an MR precursor; and the propeptide composed of 48 amino acids is cleaved and prepared into a mature MR enzyme (*J. Biol. Chem.* 264, 16862–16866 (1989)).

3. Preparation of a plasmid expressing a wild MR gene
3.1 Preparation of plasmid p2ΔB So as to construct a plasmid for expressing the MR gene in yeast, plasmid JP1 was employed as a material for preparing plasmid p2ΔB having a part of the 5' terminus of the MR gene and GAL7 promoter and GA110 terminator (FIGS. 1 through 6).

The plasmid JP1 was prepared as follows (*Mol. Gen. Genet.* 210, 462–467(1987)) (FIGS. 1 and 2): A 1.0-kb HinfI fragment was spliced out from plasmid pYF1016 having the GAL10 terminator and the GAL7 promoter (Nogi and Fukasawa, *Nucl. Acids Res.* 11, 8555(1983)) digested separately with BAL31 and NcoI, and blunt ended by polymerase reaction, and then inserted into the SmaI site of plasmid M13mp10, to produce M13mp10#39 (FIG. 1, upper left). The plasmid contains the region from the NcoI site to the A of the initiation codon ATG of the GAL7 gene of the GAL7 promoter sequence.

Alternatively, an AvaI fragment containing the MR gene was blunt ended and inserted into the blunt-ended SalI site of plasmid pSS21 which was a derivative of plasmid pJDB219, thereby generating pSS21MR. The plasmid was digested with HinfI, and the HinfI site was blunt ended by polymerase reaction, and further digested with SalI, thereby generating a 595-bp HinfI-SalI fragment. The fragment was spliced out and inserted into the M13mp10#39 which BamHI site was blunt ended prior to digestion with SalI to produce M13mp10#39MR (FIG. 1). The nucleotide sequence surrounding the ligation site between the GAL7 promoter and the MR gene is that of SEQ ID NO: 4. The AvaI fragment containing the MR gene was prepared from the plasmid pCT113 (Tonouchi et al., Nucl. Acids Res. 14, 7557 (1986)) containing the MR gene which had been isolated using a mixture of synthetic oligonucleotide probes corresponding to 208/213 amino acids from the N terminus of the MR mature protein.

Figure 2:
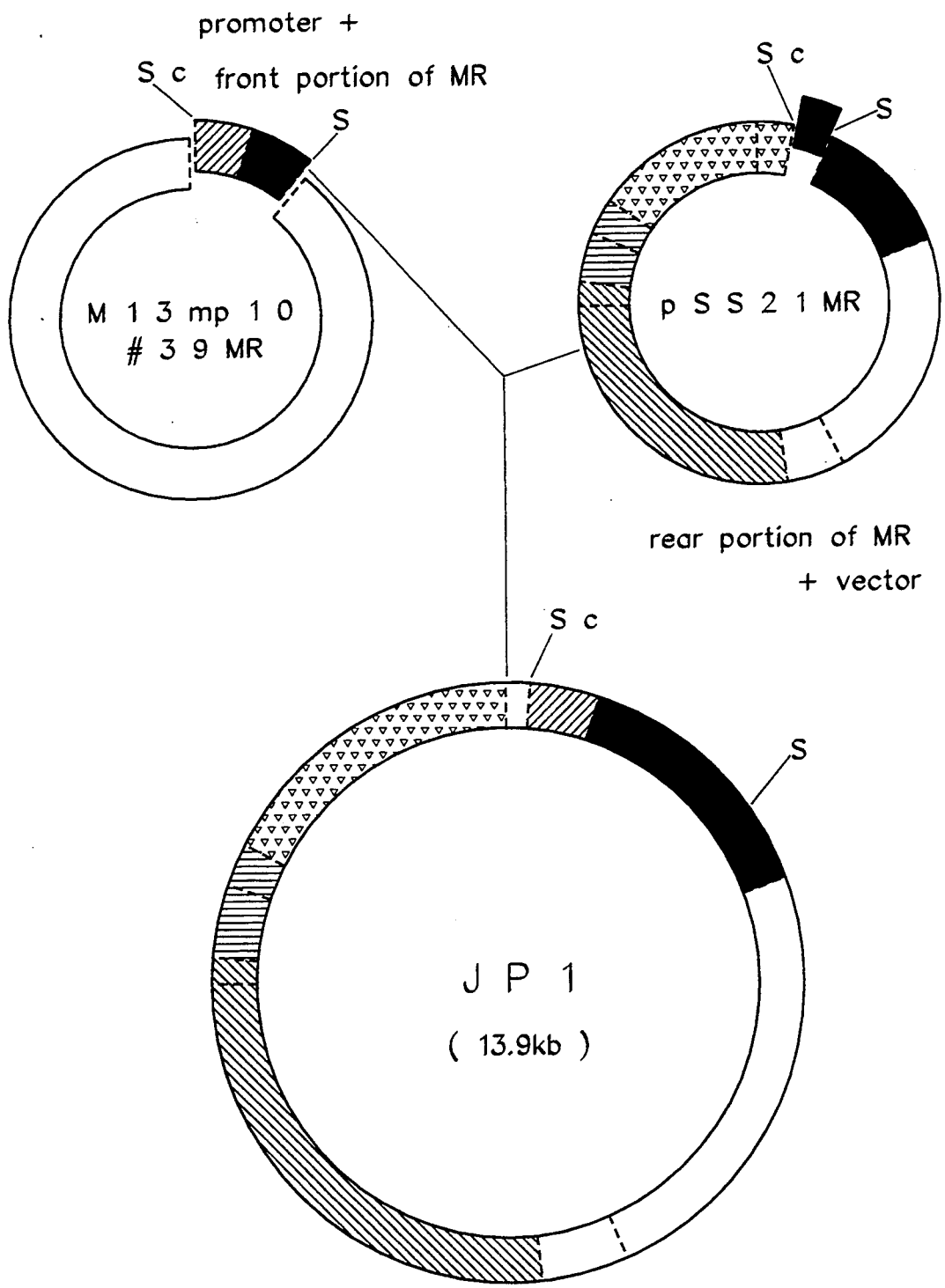
FIG. 2 depicts the process of preparing plasmid JP1 and the construction thereof.

Into the SalI and SacI sites of pSS21MR was inserted a DNA fragment of the MR gene which was ligated with the GAL7 promoter sequence upstream from the MR gene and which was obtained by digesting the M13mp10#39MR with SalI and SacI, thereby generating plasmid JP1 (FIG. 2).

JP1 DNA (10 ng) was mixed with 100 μl of the competent cell of E. coli JM109 (purchased from TAKARA SHUZO Co., Ltd.; #9052) and left on ice for 30 minutes. Following the instructions of the user's manual hereinafter, heat shock and expression were performed, and the resulting cells were spread on a plate to obtain transformant colonies next morning.

A transformant carrying the plasmid was inoculated on 200 ml of an LB medium (prepared by dissolving 10 g of Bacto peptone, 5 g of Bacto yeast extract, 5 g of NaCl, and 1 g of glucose in 1 liter of water, adjusting the resulting solution to pH 7.5 with NaOH, and sterilizing the solution), supplemented by 50 mg/l ampicillin (manufactured by Nippon Gene Co., Ltd.) in a 500-ml Sakaguchi flask and cultured at 37° C.

Fifteen hours later, the culture was centrifuged at 2,500×g for 10 minutes to recover the cells. The cells were suspended in 7.5 ml of 50 mM Tris-HCl (pH 8.0) - 25% sucrose (manufactured by WAKO Chemicals Co., Ltd.), followed by addition of 5 mg/ml lysozyme (manufactured by Sigma Co., Ltd.). The suspension was then left on ice for 5 minutes, further followed by the addition of 3 ml of 0.25M EDTA (manufactured by Dojin Chemicals Co., Ltd.), pH 8.0, which was again left on ice for 5 minutes. After addition of 3.75 ml of 5M NaCl, the resulting suspension was heated to ambient temperature.

To the suspension was added 1.5 ml of 10% SDS (sodium dodecyl sulfate: manufactured by WAKO Chemicals Co., Ltd.), and the suspension was allowed to stand on ice for more than 30 minutes, prior to centrifuge at 10,000×g at 40° C. for 10 minutes. The supernatant was recovered, followed by addition of a ¼ volume of 50% PEG 6,000 (manufactured by WAKO Chemicals Co., Ltd.), which was then left at 4° C. for 2 hours or more, prior to centrifuge at 1,500×g for 3 minutes. The supernatant was discarded to recover the precipitate.

The precipitate was dissolved in 8 ml of TE (10 mM Tris-HCl, pH 8.0, 1 mM EDTA), followed by addition of cesium chloride to a specific gravity of 1.62. Furthermore, to this solution was added 30 μl of 1% ethidium bromide (manufactured by Nippon Gene Co., Ltd.) and centrifuged at 20,000×g for 15 hours, to collect the band portion of the plasmid. The ethidium bromide was extracted and removed from the solution with cesium chloride saturated isopropanol (manufactured by WAKO Chemicals Co., Ltd.), while the cesium chloride was removed through the dialysis in TE, and thus a purified solution of the plasmid was obtained.

The plasmid JP1 DNA (10 μg) purified in such manner was digested with restriction enzyme SalI, and further digested with AccI to recover a 1.0-kb SalI-AccI fragment. In order to partially digest the fragment with a 0.2-unit restriction enzyme AluI, samples of a ⅓ volume of the original reaction mixture were taken at 5 minutes, 10 minutes and 30 minutes after the initiation of the reaction, followed by addition of phenol to terminate the enzyme reaction. These were pooled and subjected to electrophoresis to recover 0.88-kb fragments.

Then, 4 μg of the plasmid M13mp10#39MR was digested with restriction enzymes SalI and EcoRI to recover 1.1-kb fragments.

Furthermore, 0.5 μg of ampicillin resistant gene-containing plasmid pBR322 (purchased from Nippon Gene Co., Ltd.) was digested with restriction enzyme BamHI prior to blunt ending, followed by digestion with restriction enzyme EcoRI. The resulting plasmid was subjected to electrophoresis on agarose gel to recover 4.0-kb fragments.

Figure 3:
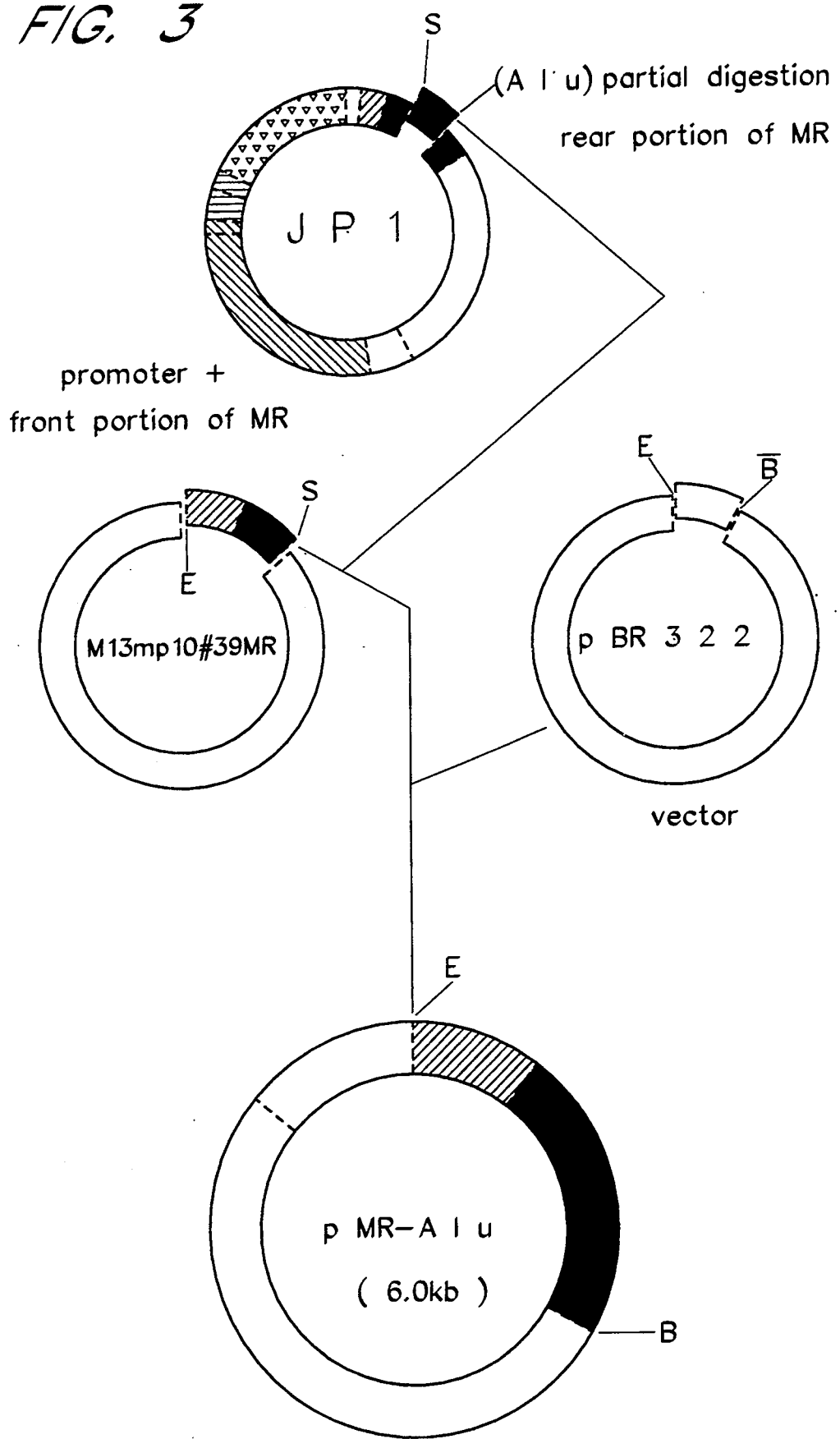
FIG. 3 depicts the process of preparing plasmid pMR-Alu.
Figure 4:
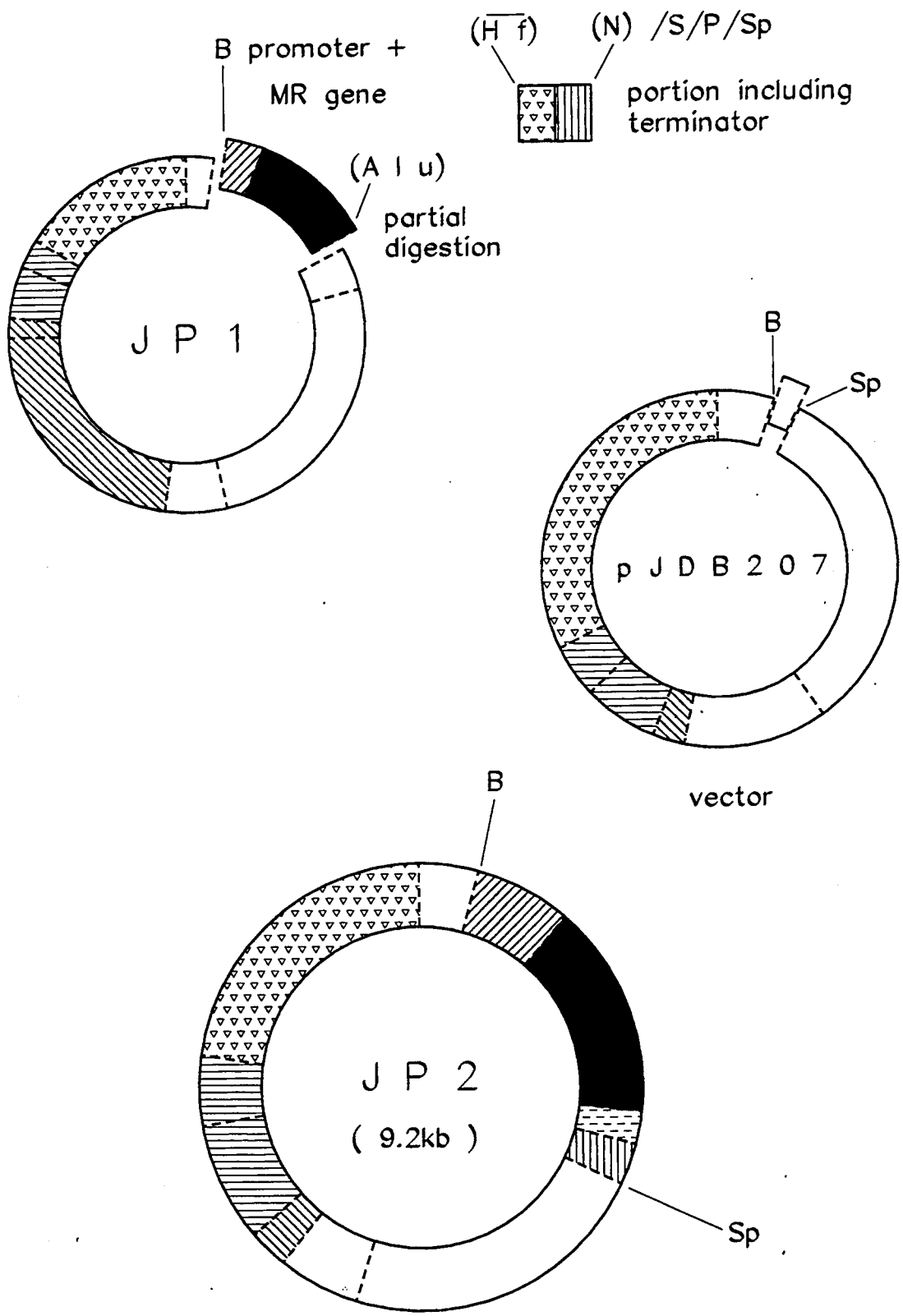
FIG. 4 depicts the process of preparing plasmid JP2.

Three fragments of 0.88 kb, 1.1 kb and 4.0 kb thus obtained were ligated together and then introduced to E. coli JM109. Some of the colonies grown on the ampicillin containing plates were selected, and from them was prepared DNA. By restriction enzyme digestion analysis, a plasmid putatively identified to have the desired construction was selected and designated as pMR-Alu (FIG. 3).

Alternatively, the following three fragments were ligated together to prepare a plasmid JP2 carrying GAL7 promoter, the whole length of the MR gene and GAL10 terminator, and further carrying the LEU2 gene and the Ap$^r$ gene at the site of the vector (Mol. Gen. Genet. 210, 462–467(1987)) (FIG. 4):

(1) a vector sequence obtained by digesting a yeast plasmid YEp13 derivative, pJBD207, with BamHI and SphI;

(2) a fragment with a truncated region of GAL7 promoter and the 3' non-coding region of the MR gene, which was obtained by subjecting JP1 to limited digestion with AluI and digestion with BamHI; and (3) a fragment obtained by splicing a 0.42-kb HinfI-NcoI fragment containing the downstream portion of GAL10 gene and the terminator from the plasmid pYF1016 (described above) carrying GAL10 terminator and the GAL7 promoter sequence, ligating a SalI/PstI/SphI polylinker to the fragment, digesting the 3' terminus of the fragment with SphI, while digesting the 5' terminus thereof with HinfI, and thereafter blunt ending the termini.

The DNA (8 μg) of the plasmid JP2 thus prepared was digested with restriction enzyme HincII, and 0.2-kb fragments were recovered by agarose gel electrophoresis. The fragments were further digested with restriction enzyme AccI and blunt ended to recover 0.2-kb fragments by agarose gel electrophoresis.

After digesting 0.2 μg of plasmid pBR322 with restriction enzymes BamHI and AccI, the termini were blunt ended to obtain 4.1-kb fragments.

Figure 5:
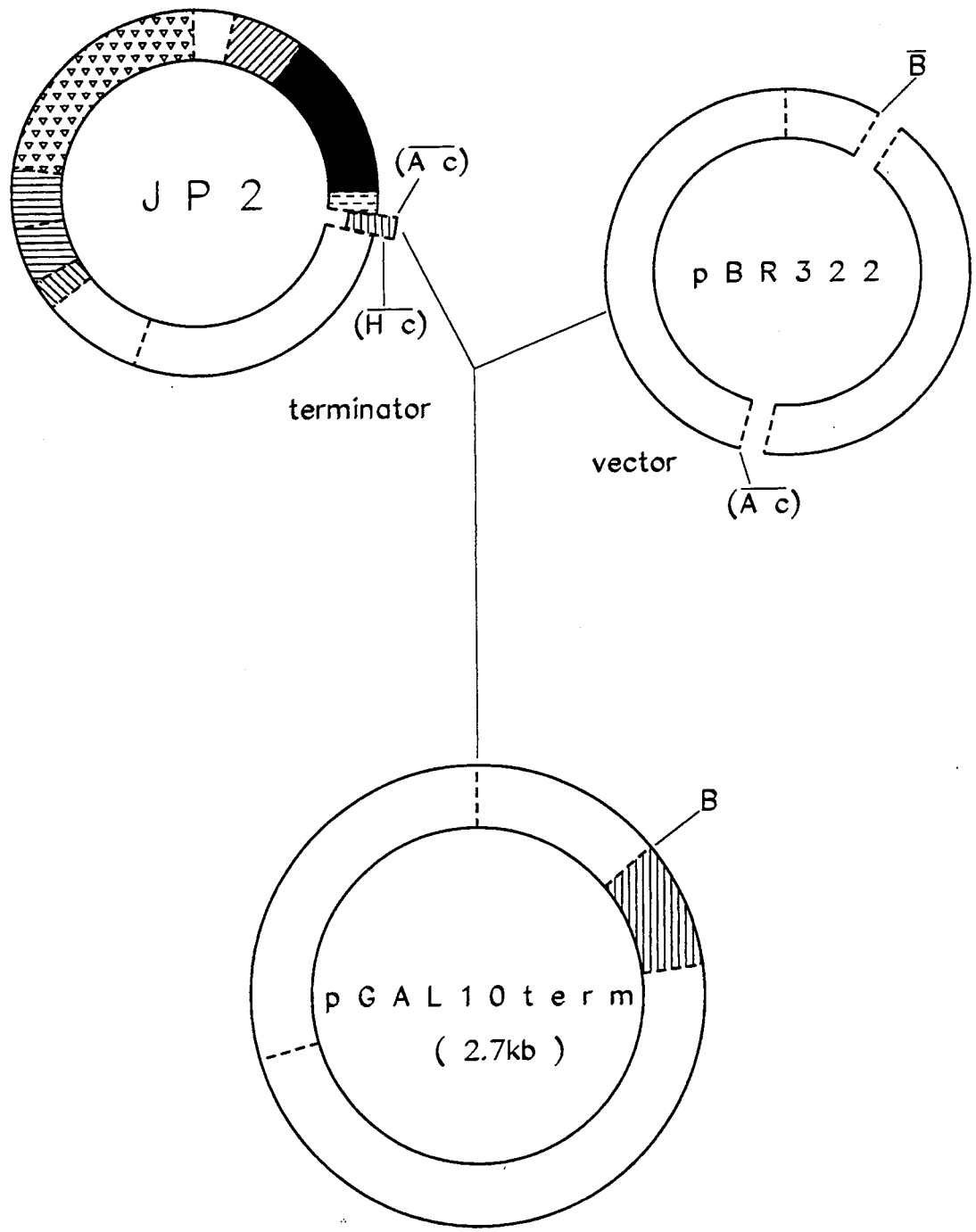
FIG. 5 depicts the process of preparing plasmid pGAL10term.

These two fragments of 0.2 kb and 4.1 kb were ligated together and introduced into E. coli JM109. A plasmid having a recoginition site of restriction enzyme BamHI where GAL10 terminator was inserted in clockwise direction was selected and designated as pGAL10term (FIG. 5).

Figure 6:
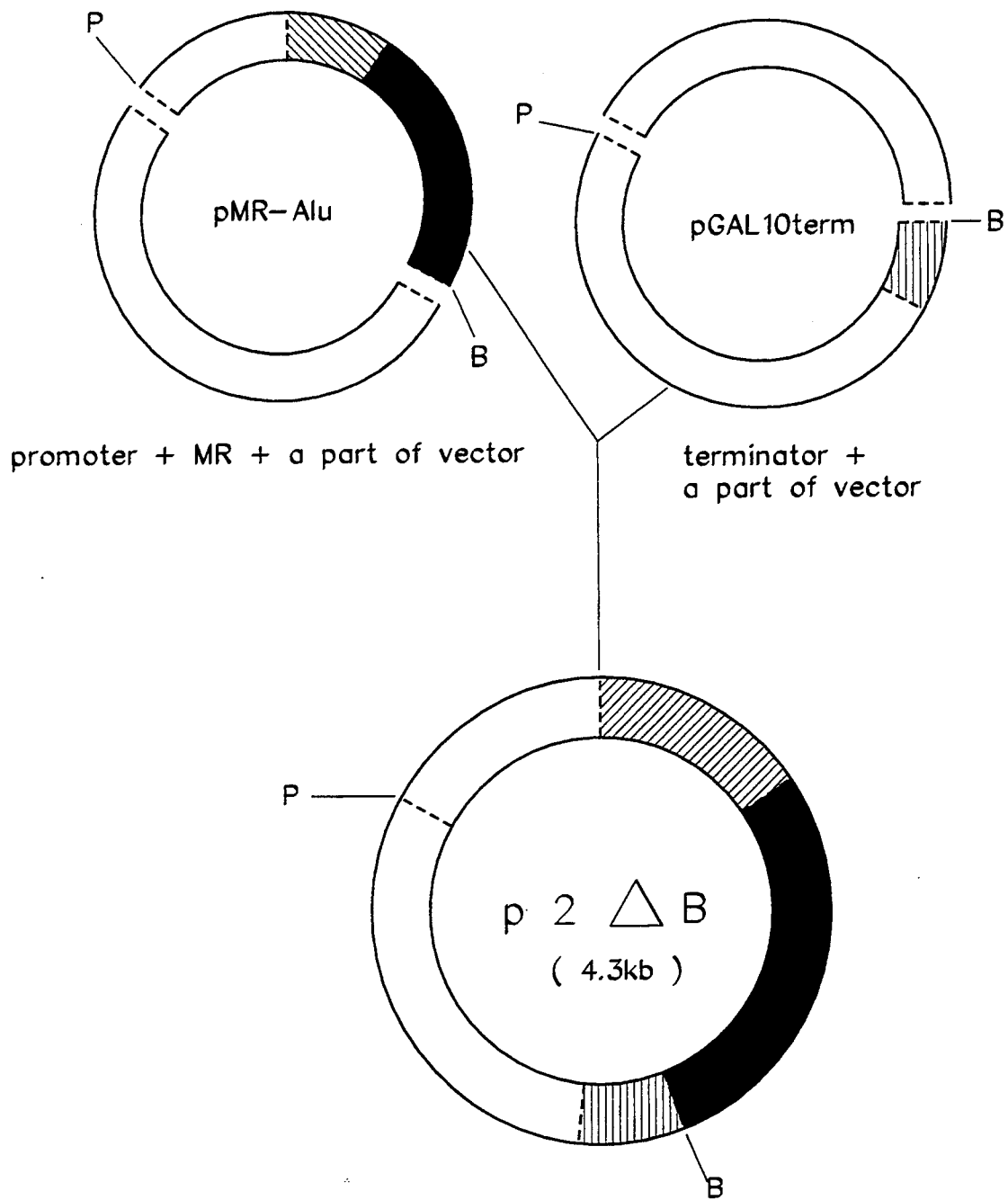
FIG. 6 depicts the process of preparing plasmid p2ΔB.

0.5 μg each of pMR-Alu and pGAL10term were digested with restriction enzymes BamHI and PstI to recover 2.7-kb and 1.6-kb fragments, respectively. These were ligated together, and introduced into *E. coli* JM109, to obtain a plasmid which was designated as p2ΔB (FIG. 6).

3.2 Preparation of plasmid JS3

Figure 7:
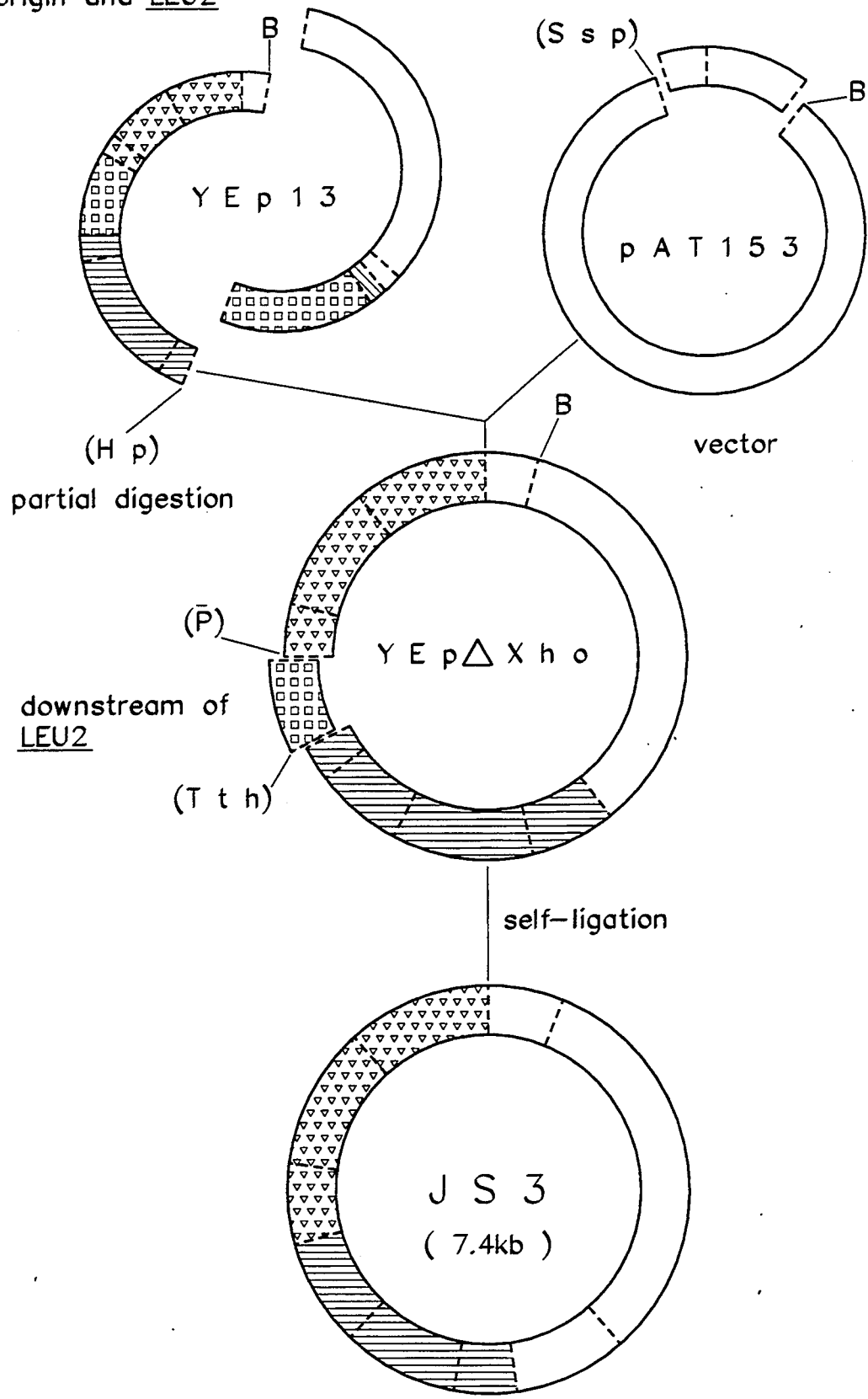
FIG. 7 depicts the process of preparing plasmid JS3.

A small plasmid JS3 carrying the LEU2 gene complementary to the leucine requirement of the yeast MC16 strain and capable of replication both in yeast and *E. coli*, was prepared as follows (FIG. 7).

Plasmid YEp13 (J. R. Broach et al. *Gene* 9, 287 (1980)) (1 μg) was digested with restriction enzyme BamHI. Then, for partial digestion with 0.2-unit of restriction enzyme HpaI, samples of a ⅓ volume of the solution were taken at 5 minutes, 10 minutes and 30 minutes after the initiation of the reaction, followed by phenol extraction. These were pooled and subjected to electrophoresis on agarose gel to recover 5.0-kb fragments.

Alternatively, 0.5 μg of plasmid pAT153 (purchased from Biores B. V.) was digested with restriction enzymes BamHI and SspI to recover 3.1-kb fragments.

These two fragments of 5.0 kb and 3.1 kb were ligated together to generate a plasmid YEpΔXho.

One microgram each of YEpΔXho was digested with restriction enzyme PstI or TthIII-I, prior to repairing of the termini. These were further digested with restriction enzyme BamHI to recover 2.4-kb and 5.1-kb fragments. These two fragments were ligated together to generate a plasmid JS3.

3.3 Preparation of plasmid JS5

Figure 8:
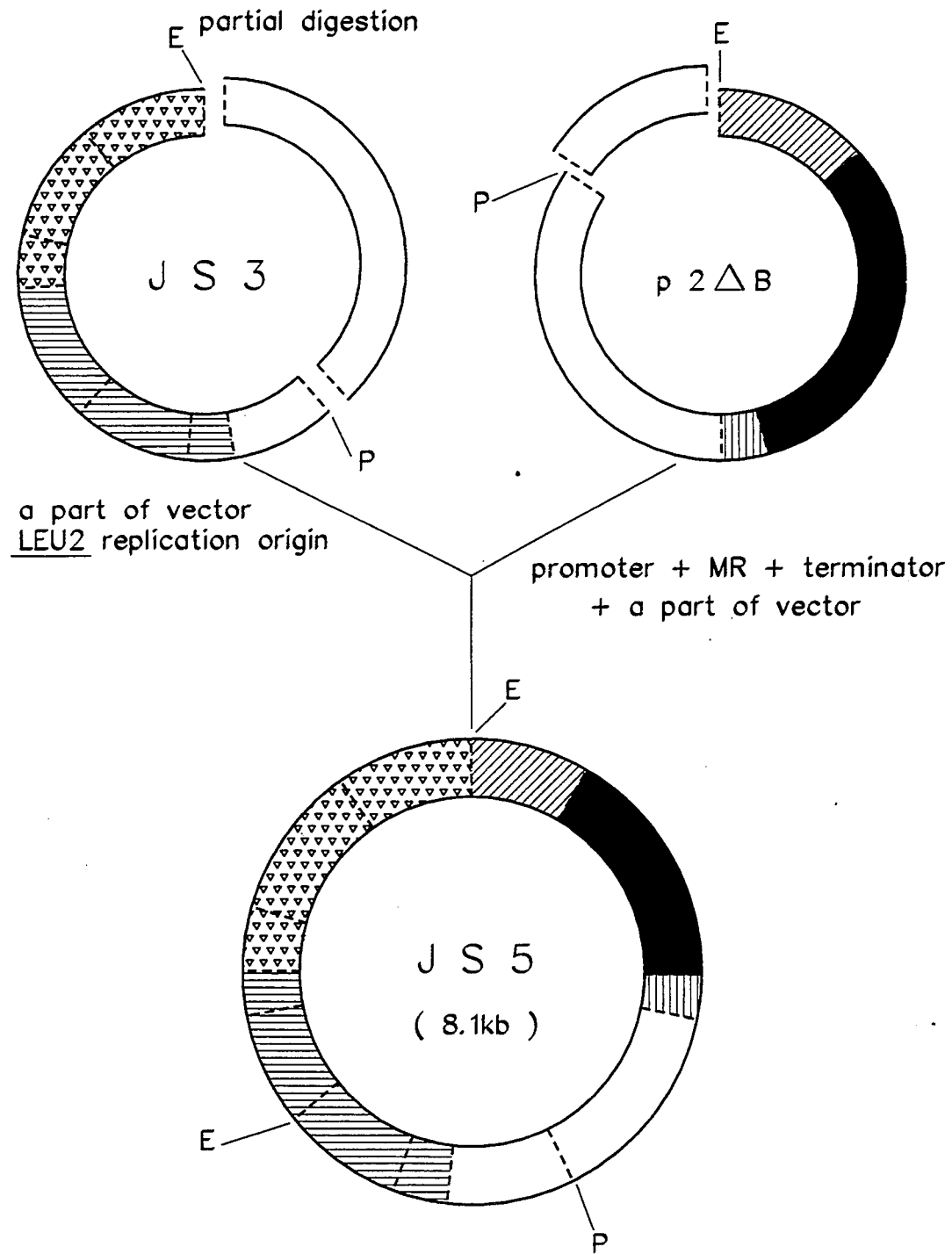
FIG. 8 depicts the process of preparing plasmid JS5.

Two micrograms of the plasmid JS3 were digested with restriction enzyme PstI, and partially digested with restriction enzyme EcoRI, thereafter recovering 2.5-kb fragments. Then, 1 μg of plasmid p2ΔB was digested with restriction enzymes PstI and EcoRI to recover 3.5-kb fragments. By ligating these two fragments together, a plasmid vector JS5 was obtained, which can produce and secret wild MR during the cultivation of the yeast (FIG. 8) under the control of GAL7 promoter.

4. Preparation of mutant MR-expressing plasmid

Figure 9:
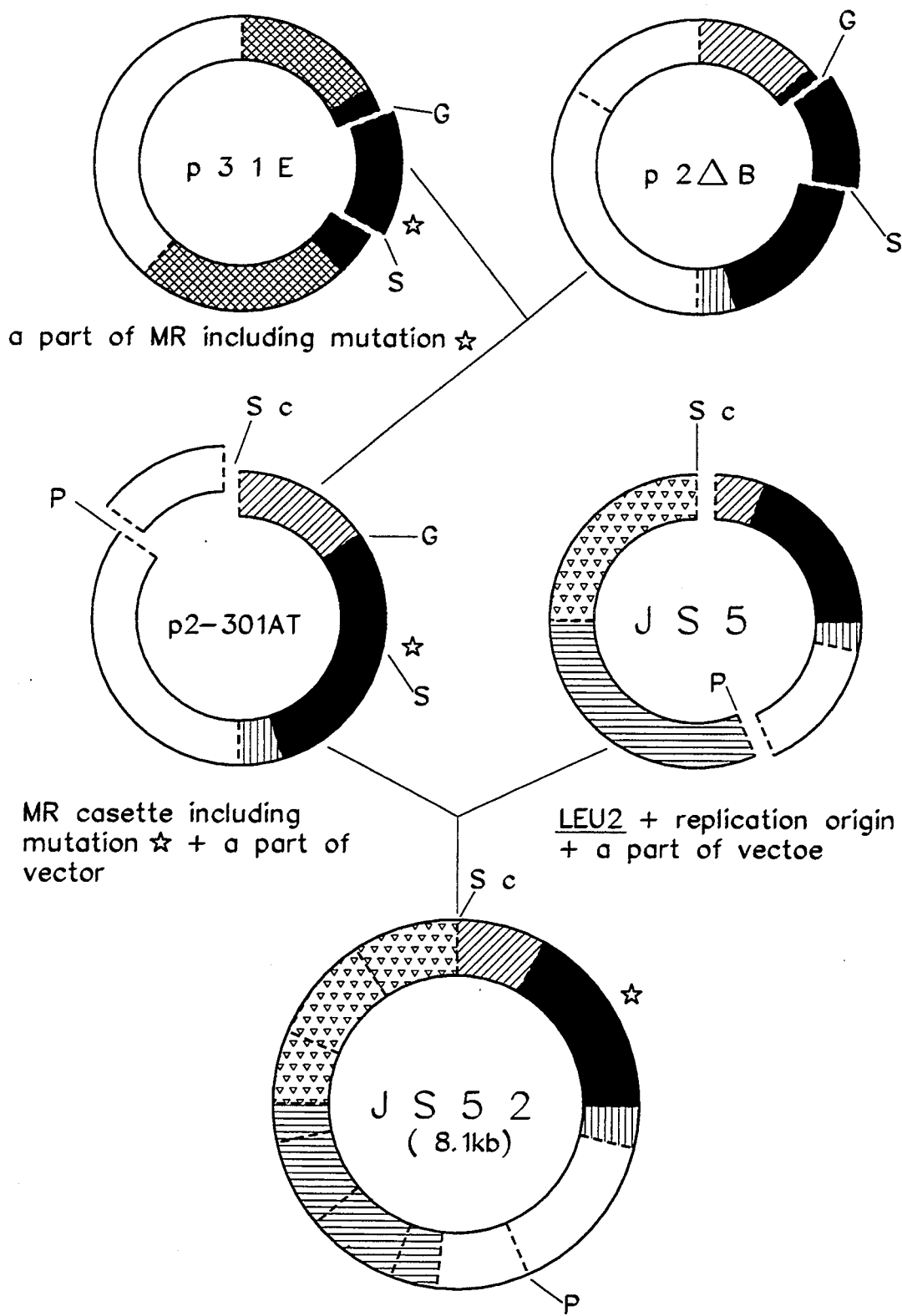
FIG. 9 depicts the process of preparing plasmid JS52.
Figure 10:
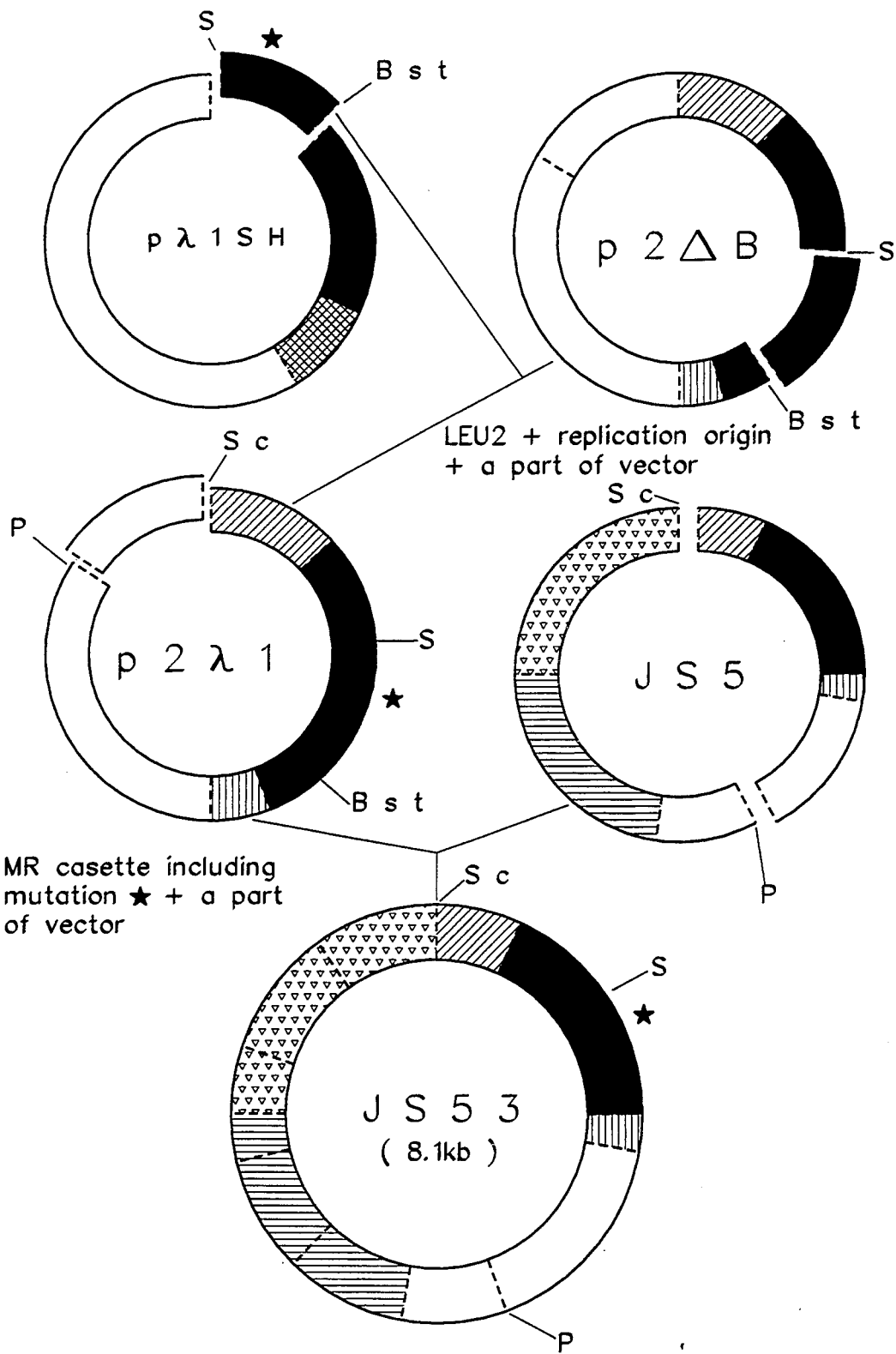
FIG. 10 depicts the process of preparing plasmid JS53.
Figure 11:
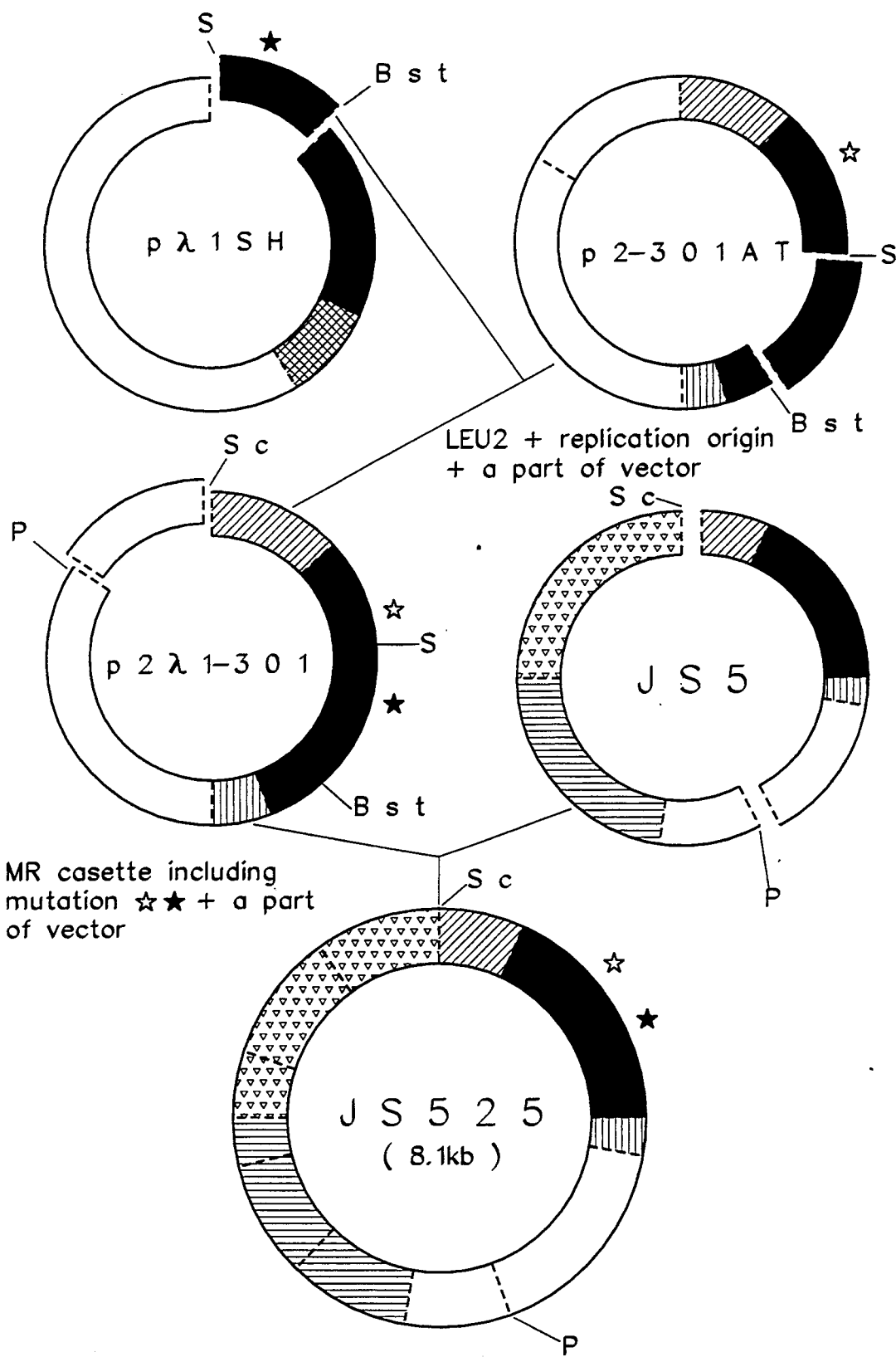
FIG. 11 depicts the process of preparing plasmid JS525.

By using the wild MR gene-expressing plasmid obtained above, a plasmid expressing the mutant MR gene was prepared (FIGS. 9 through 11).

By ligating a 0.5-kb fragment obtained by digesting 2 μg of the mutant MR gene-carrying plasmid p31E with restriction enzymes SalI and BglII with a 3.8-kb fragment obtained by similarly digesting 0.5 μg of the wild MR-expressing plasmid p2ΔB with restriction enzymes SalI and BglII, plasmid p2-301AT was obtained (FIG. 9, upper left).

By ligating a 3.5-kb fragment obtained by digesting 2 μg of the p2-301AT with restriction enzymes SacI and PstI with a 4.4-kb fragment obtained by digesting 2 μg of the plasmid JS5 with restriction enzymes SacI and PstI, plasmid JS52was obtained (FIG. 9).

In a similar manner, a fragment obtained by digestion of plasmid pλ1SH with restriction enzymes SalI and BstPI was substituted for a corresponding fragment of p2ΔB or p2-301AT to obtain a plasmid which was designated as p2λ1 (FIG. 10, middle left) or p2λ-301 (FIG. 11, middle left).

Following the same procedure as in the preparation of JS52, a 3.5-kb fragment obtained by digestion of each plasmid described above with restriction enzymes SacI and PstI was ligated with a 4.4-kb SacI-PstI fragment of JS5. The resulting plasmid was designated as plasmid JS53 (FIG. 10) or JS525 (FIG. 11).

Of these plasmids, JS52 has a gene coding for a protease wherein amino acid 101 of the amino acid sequence represented by SEQ ID NO:2 is substituted by threonine; JS53 has a gene coding for a protease wherein amino acid 186 of the amino acid sequence represented by SEQ ID NO:2 is substituted by aspartic acid; and JS525 has a gene coding for a protease wherein amino acids 101 and 186 of the amino acid sequence represented by SEQ ID NO:2 are substituted by threonine and aspartic acid, respectively; and these plasmids individually have a promoter that can express MR gene in *Saccharomyces cerevisiae*, and are replicable in *Saccharomyces cerevisiae*.

5. MR Production in yeast

GAL7 promoter capable of strict induction and regulation of expression has conventionally been used, so as to generate and secrete MR efficiently from yeast transformants (Nogi and Fukasawa, *Nucl. Acids Res.* 11, 8555–8568 (1983)). This is a promoter which can be induced by galactose in a medium without glucose. In accordance with the present invention, this promoter may be used as well.

Yeast transformation, expression of the MR gene using GAL7 promoter and purification of the MR protein will now be described hereinbelow.

5.1 Transformation of Yeast

Yeast MC16 strain cultured overnight in a YPD medium (1% yeast extract, manufactured by DIFCO Laboratories, U.S.A., 2% Bacto peptone, manufactured by DIFCO Laboratories, U.S.A., 2% glucose) was inoculated at 10% in a fresh YPD medium, and cultured at 30° C. for 4 hours. The culture broth (1.5 ml) was mildly centrifuged with a bench-top centrifuge to collect the cells, followed by rinsing in 0.2M LiSCN (manufactured by Kanto Chemical Co., Ltd.). The resulting cells were then suspended in 0.02 ml of 1M LiSCN.

0.01 ml (about 3 μg) of each plasmid solution of JS5, JS52, JS53 and JS525, and 0.03 ml of 70% PEG 4,000 (manufactured by WAKO Chemical Co., Ltd.) were added to and mixed with the suspension, and kept at 30° C. for one hour. To the resulting solution was added 0.14 ml of sterile water for dilution, and this solution was then plated on two SDah plates (0.67% Bacto-yeast nitrogen base w/o amino acid (manufactured by Difco Laboratories, U.S.A.) 2% glucose, 0.002% adenine sulfate, 0.002% L-histidine-HCl (manufactured by WAKO Chemical Co., Ltd.), and 2% agar). The plates were incubated at 30° C. for 2 to 3 days, thereby generating a transformant.

5.2 Expression of MR gene by a transformant

In 50 ml of the YPD medium in a 500-ml Sakaguchi flask, the shake culture of the transformant thus obtained was performed at 30° C. for 2 days, to proliferate the cells. The cells were collected by centrifugation at 1,000×g for 5 minutes, and resuspended in 100 ml of a YPGal medium (1% yeast extract, 2% Bacto peptone, 4% galactose (manufactured by WAKO Chemicals Co., Ltd.)). The suspension was subjected to shake culture in a 500-ml Sakaguchi flask at 30° C. for 3 days. The MCA of the culture supernatant was determined by placing 2 μl of the supernatant on a skim milk plate (1% skim milk (purchased from DIFCO Laboratories, U.S.A.), 100 mM acetate buffer, pH 5.2, 1% agar), keeping the plate at 37° C. for 10 minutes, and detecting halo formation.

5.3 Purification of MR protein

The culture broth was centrifuged at 1,000×g for 10 minutes, and the resulting supernatant of 200 ml was diluted two-fold with 20 mM sodium acetate, pH 6.0–5 mM EDTA buffer, which was then passed through 30 ml of an ion exchanger DEAETOYOPEARL 650M (manufactured by TOSOH Co., Ltd.) equilibrated with the same buffer in order that MR protein might be adsorbed onto the ion exchanger. After washing the column with the same buffer, the MR protein was subsequently eluted with the same buffer supplemented with 0.4M NaCl. The MR protein containing fractions were detected by the skim milk plate method described above.

The active fraction thus obtained was concentrated through an ultra-filtration membrane purified by high performance liquid chromatography on a gel filtration column G3000SW (manufactured by TOSOH Co., Ltd.). The protein in the active fraction was detected on SDS-PAGE (a product manufactured by TEF Corporation was used as the gel), which showed a single band.

6. Preparation of site-specific mutant MR gene

As has been described above, the glycine at position 186 is mutated into aspartic acid in one of the mutant MRs with reduced thermostability. In order to demonstrate that the mutation of the amino acid at this position has a great effect on the reduction of the thermostability, the substitution by a number of other amino acids has been attempted. The method therefor and the results are shown below. Site-directed mutagenesis was performed by the Kunkel method.

6.1 Preparation of a synthetic primer

Firstly, it was synthesized a 20-mer single stranded DNA encoding an amino acid sequence including an amino acid to be mutated and the region proximate to said amino acid. The sequence is represented by SEQ ID NO:3, provided that a position occupied by any of A, C, G and T is represented by N. The sequence corresponds to a sequence coding 183/188 amino acids. Based on the sequence, the mutation of amino acid 186 into 15 types of amino acids excluding tryptophan, methionine, lysine, glutamine and glutamic acid can be expected theoretically.

The synthetic DNA was synthesized by $\beta$-cyanoethyl amidite method, using a DNA synthesizer, Cyclone Plus DNA, manufactured by the Milligen/Biosearch Division of MILLIPORE, and the purification thereof was performed by acetonitrile gradient elution from a reverse phase column, Inertsil ODS-2 (manufactured by GL Science Co., Ltd.), both prior to and after the dedimethyltrityl process.

After purification, 1.5 nmol of the synthetic primer was dissolved in 0.05 ml of a buffer (0.07M Tris-HCl, pH 7.5, 5 mM $MgCl_2$, 5 mM dithiothreitol (manufactured by WAKO Chemical Co., Ltd.), 1 mM ATP (manufactured by TAKARA SHUZO Co., Ltd.)), followed by addition of 10-unit T4 polynucleotide kinase for reaction at 37° C. for one hour to phosphorylate the termini.

6.2 Introduction of a mutation and subcloning the mutantgene into M13

A fragment obtained by digesting 1 $\mu$g of plasmid p2$\Delta$B with restriction enzymes KpnI and BamHI was ligated with 0.1 $\mu$g of M13mp19 RF DNA cleaved with the same enzymes, to obtain a phage DNA containing a part of the MR gene. The recombinant RF DNA is referred to as MRKB/mp19.

The MRKB/mp19 was introduced into E. coli BW313 (purchased from TAKARA SHUZO Co., Ltd.). The resulting transformant was cultured to obtain a phage, which was then subjected to PEG precipitation and phenol treatment to generate a single stranded DNA. Some of the thymines of the DNA are modified into deoxyuracil due to the mutation in E. coli BW313. The DNA containing deoxyuracil is not replicable in usual E. coli strains.

Mutan-K kit (manufactured by TAKARA SHUZO Co., Ltd.) was used to perform site-directed mutagenesis. Following the supplier's instruction, 0.2 pmol of the single stranded DNA containing deoxyuracil was annealed with 1 pmol of the synthetic DNA. Then, a buffer containing 1-unit T4 DNA polymerase, 50-unit of E. coli DNA ligase and NAD and four types of nucleotides (dNTPs) was added to the annealed product, which was then kept at 25° C. for 2 hours, to synthesize and cycle the complementary chain.

The resulting DNA was then introduced into E. coli BMH71-18 mutS in which no induction of reverse mutation is likely to occur, to form plaques using E. coli MV1184 as an indicator bacterium. Phages isolated from some of the plaques were cultured, and a single stranded DNA was subsequently prepared for the determination of the nucleotide sequence to confirm the presence of mutant genes.

Consequently, the mutant genes obtained were classified in a total of seven types, wherein the amino acid 186 was modified in six species of amino acids, namely, Ala(GCC), Cys(TGC), Ile(ATC), Ser(AGC), Arg(CGC), and Val(GTC) and in the same expression type as in JS53 (Asp: the same amino acid as in JS53, but the codon is GAC).

E. coli individually infected with these mutant phages were cultured to prepare RF DNAs in the same manner as in the plasmid preparation. These six types of the replicative-form DNAs were cleaved with restriction enzymes KpnI and BamHI, producing 1-kb fragments. 1 $\mu$g of each of these fragments was ligated with 0.3 $\mu$g each of 3.3-kb fragments obtained by digesting plasmid p2$\Delta$B with the same enzymes, to generate six types of plasmids pMRX-A, pMRX-C, pMRX-I, pMRX-S, pMRX-R, and pMRX-V.

Then, 1.5 $\mu$g of each of the 2.1-kb fragments obtained by digesting these six types of plasmids with restriction enzymes SacI and BamHI was ligated with 0.5 $\mu$g of the 6.1-kb fragments generated by digestion of plasmid JS5 with the same enzymes, thereby generating plasmids JS53A, JS53C, JS53I, JS53S, JS53R and JS53V.

These plasmids have a gene coding for a protease whose amino acid sequence is represented by SEQ ID NO:2, wherein amino acid 186 of the amino acid sequence is substituted by an amino acid other than glycine. This glycine residue is substited with alanine in JS53A, cysteine in JS53C, isoleucine in JS53I, serine in JS53S, arginine in JS53R and valine in JS53V.

These replicable plasmids have GAL7 promoter which can function in Saccharomyces cerevisiae. These plasmids were introduced into yeast MC16 in the same manner as in JS52, JS53 and JS525.

The transformants individually carrying JS52, JS53, and JS525 are deposited as Accession Numbers FERM BP3898, BP3900 and BP3899, respectively, with the Patent Microorganism Depository, Fermentation Research Institute, Agency of Industrial Science and

6.3 Properties of mutant enzymes

The mutant enzymes produced by the strains above were prepared in the same manner as in section 5.2 "Expression of MR gene by a transformant". Examination was performed into the properties of the enzymes produced by the yeast transformants carrying the individual mutant plasmids.

The molecular weight was determined based on the results of electrophoresis on 12% SDS-PAGE (the gel is manufactured by TEF Corporation).

The thermostability was determined based on the remaining activity in % after heating in 20 mM phosphate buffer (pH 6.2) at 55° C. for 15 minutes.

The pH profile of milk clotting activity was determined based on the clotting time of 10% skim milk dissolved in 20 mM phosphate buffer, pH 5.5 to 7.0, containing 10 mM $CaCl_2$.

The proteolytic activity was determined on the basis of the amount of the protein which was rendered soluble in an aqueous 2.5% trichloroacetic acid solution by the reaction using casein (manufactured by DIFCO Laboratories, U.S.A.) as the substrate.

TABLE 1

| Vector (A.A.101, A.A. 186)[1] | thermo-stability (%) | Optimum pH | Molecular weight, KDa | C/P[2] |
|---|---|---|---|---|
| JS52 (Thr, Gly) | 5.4 | 5.5–5.8 | 48 | 1.08 |
| JS53 (Ala, Asp) | 1.2 | 5.5–5.8 | 48 | 0.93 |
| JS525 (Thr, Asp) | <0.6 | 5.5–5.8 | 48 | 1.03 |
| JS53A (Ala, Ala) | 9.8 | 5.5–5.8 | 48 | 0.86 |
| JS53C (Ala, Cys) | 1.4 | 5.5–5.8 | 48 | 0.57 |
| JS53I (Ala, Ile) | <1.2 | 5.5–5.8 | 48 | 0.55 |
| JS53S (Ala, Ser) | 9.7 | 5.5–5.8 | 48 | 0.94 |
| JS53R (Ala, Arg) | <0.6 | 5.5–5.8 | 48 | 0.93 |
| JS53V (Ala, Val) | <0.9 | 5.5–5.8 | 48 | 0.69 |

[1] amino acids at 101 and 186
[2] milk clotting activity/proteolytic activity (a relative value to the value of JS5 which is defined as 1).

As shown in Table 1, all of the mutant enzymes showed more reduced thermostability than the wild MR, which clearly indicates that amino acid 186 exerts strong effect on the thermostability. The aspartic acid at this position putatively has an important function for retaining the steric conformation of MR.

Because other mutant enzymes produced by mutant plasmids excluding JS53A and JS53S showed lower thermostability than the enzyme produced by JS52 with a mutation at amino acid 101, the mutation at amino acid 186 is possibly more effective in the reduction of thermostability. Nevertheless, the mutation at amino acid 101 is also important because a doubly mutant enzyme having both of the mutations (generated by JS525) has a lower thermostability.

Figure 12:
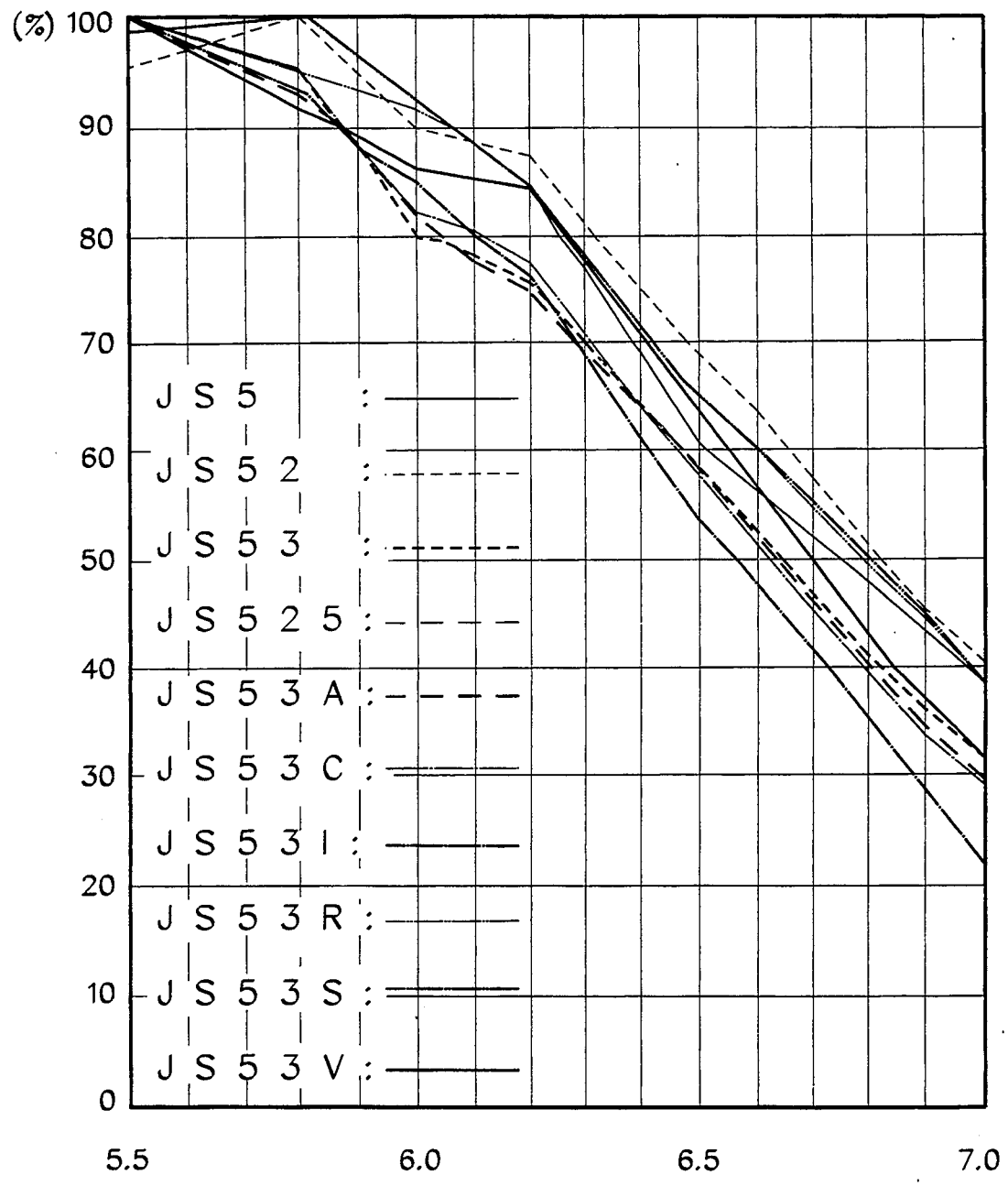
FIG. 12 depicts the pH profiles of the milk clotting activities of a wild enzyme and a mutant enzyme.

The pH profile and molecular weight of each of the mutant enzymes do not show a significant difference from those of the wild enzymes (FIG. 12) so that the mutant enzymes may possibly have the properties required for protease.

Thus, nine kinds of the mutant MRs with the reduced thermostability were successfully prepared. Furthermore, the gene thereof and the plasmids expressing the gene, and the yeast strains producing the individual mutant enzymes were successfully prepared.

Furthermore, the mutant MR productivity of such yeast strains was comparative to that of the *Mucor pusillus* mutant strain.

---

What is claimed is:

1. An isolated protease having an amino acid sequence represented by amino acid numbers from 1 to 361 in SEQ ID NO:2, wherein amino acid 101 is substituted by threonine.

2. An isolated protease as defined in claim 1, wherein amino acid 186 of said amino acid sequence is substituted by aspartic acid.

3. An isolated protease having an amino acid sequence represented by amino acid numbers from 1 to 361 in SEQ ID NO:2, wherein amino acid 186 is substituted by an amino acid selected from the group consisting of aspartic acid, alanine, cysteine, isoleucine, serine, arginine and valine.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 2009 bases
        ( B ) TYPE: nucleic acid
        ( C ) STRANDEDNESS: double
        ( D ) TOPOLOGY: linear ( i i ) MOLECULE TYPE: Genomic DNA ( i i i ) HYPOTHETICAL: NO ( i v ) ANTI-SENSE: NO ( v i i ) IMMEDIATE SOURCE:
        ( B ) CLONE: IF04578()

( i x ) FEATURE:
        ( A ) NAME/KEY: CDS
        ( B ) LOCATION: 361 to 1641

( x i ) SEQUENCE DESCRIPTION: SEQ ID NO:1:

```
AATCGGGCAT TGTACAGCGT TTTACCGATC TAAATGACTG TATTCGAGAG AAAGTGGAAA    60

GAGTGGTGTT ATGCATTAGA TGTTACAAGT TCATGCCATA GGTGACACAC ACAATTTCTG   120

CCTTTTTATG ACTTTGTCTG TTTAATCAAT ATGGTAATAC ACCCCGCGGT CCAAGGCAGT   180
```

```
ACCCAGTCTT GCAAACACCT TTCCAGGTAA AATCATACAA TTATGGACTC TAACGTTTTT    240

CAAAATGTCA ATTTTGCAGA CGAACGGCAC ACAGATCTTC TAGTGGCCAA ACTGCGTAGA    300

TCCCTTTTTC ATATAAAACC AGCCGGATGC GAGACTCTGA GACCTCATCA AATCCTCAAC    360
```

| ATG | CTC | TTC | TCC | AAG | ATC | TCC | TCT | GCA | ATC | CTT | TTG | ACC | GCT | GCT | TCT | 408 |
|---|---|---|---|---|---|---|---|---|---|---|---|---|---|---|---|---|
| Met | Leu | Phe | Ser | Lys | Ile | Ser | Ser | Ala | Ile | Leu | Leu | Thr | Ala | Ala | Ser | |
| | | | | -65 | | | -60 | | | | -55 | | | | | |

| TTT | GCA | CTT | ACC | AGT | GCT | CGC | CCA | GTA | TCC | AAG | CAA | TCT | GAT | GCC | GAT | 456 |
|---|---|---|---|---|---|---|---|---|---|---|---|---|---|---|---|---|
| Phe | Ala | Leu | Thr | Ser | Ala | Arg | Pro | Val | Ser | Lys | Gln | Ser | Asp | Ala | Asp | |
| -50 | | | | | -45 | | | | | -40 | | | | | -35 | |

| GAC | AAG | CTA | TTG | GCT | CTT | CCC | TTG | ACA | TCC | GTC | AAC | CGC | AAA | TAC | TCT | 504 |
|---|---|---|---|---|---|---|---|---|---|---|---|---|---|---|---|---|
| Asp | Lys | Leu | Leu | Ala | Leu | Pro | Leu | Thr | Ser | Val | Asn | Arg | Lys | Tyr | Ser | |
| | | | | -30 | | | | | -25 | | | | | -20 | | |

| CAA | ACC | AAA | CAC | GGA | CAG | CAG | GCT | GCC | GAA | AAA | TTG | GGC | GGT | ATC | AAG | 552 |
|---|---|---|---|---|---|---|---|---|---|---|---|---|---|---|---|---|
| Gln | Thr | Lys | His | Gly | Gln | Gln | Ala | Ala | Glu | Lys | Leu | Gly | Gly | Ile | Lys | |
| | | | -15 | | | | | -10 | | | | | -5 | | | |

| GCG | TTC | GCT | GAG | GGA | GAT | GGT | TCC | GTT | GAT | ACA | CCT | GGC | TTG | TAC | GAC | 560 |
|---|---|---|---|---|---|---|---|---|---|---|---|---|---|---|---|---|
| Ala | Phe | Ala | Glu | Gly | Asp | Gly | Ser | Val | Asp | Thr | Pro | Gly | Leu | Tyr | Asp | |
| | | | 1 | | | | 5 | | | | | 10 | | | | |

| TTT | GAC | TTG | GAG | GAG | TAC | GCC | ATT | CCA | GTT | TCC | ATC | GGT | ACT | CCT | GGA | 648 |
|---|---|---|---|---|---|---|---|---|---|---|---|---|---|---|---|---|
| Phe | Asp | Leu | Glu | Glu | Tyr | Ala | Ile | Pro | Val | Ser | Ile | Gly | Thr | Pro | Gly | |
| 15 | | | | | 20 | | | | | 25 | | | | | 30 | |

| CAA | GAC | TTT | TAT | CTT | TTG | TTC | GAT | ACC | GGC | AGT | TCC | GAT | ACT | TGG | GTT | 696 |
|---|---|---|---|---|---|---|---|---|---|---|---|---|---|---|---|---|
| Gln | Asp | Phe | Tyr | Leu | Leu | Phe | Asp | Thr | Gly | Ser | Ser | Asp | Thr | Trp | Val | |
| | | | | 35 | | | | | 40 | | | | | 45 | | |

| CCC | CAC | AAA | GGC | TGC | GAT | AAC | TCT | GAG | GGC | TGC | GTT | GGC | AAA | CGC | TTC | 744 |
|---|---|---|---|---|---|---|---|---|---|---|---|---|---|---|---|---|
| Pro | His | Lys | Gly | Cys | Asp | Asn | Ser | Glu | Gly | Cys | Val | Gly | Lys | Arg | Phe | |
| | | | 50 | | | | | 55 | | | | | 60 | | | |

| TTC | GAT | CCT | TCC | TCT | TCT | TCC | ACC | TTC | AAA | GAA | ACC | GAC | TAC | AAC | CTG | 792 |
|---|---|---|---|---|---|---|---|---|---|---|---|---|---|---|---|---|
| Phe | Asp | Pro | Ser | Ser | Ser | Ser | Thr | Phe | Lys | Glu | Thr | Asp | Tyr | Asn | Leu | |
| | | 65 | | | | | 70 | | | | | 75 | | | | |

| AAC | ATC | ACC | TAC | GGT | ACC | GGC | GGT | GCT | AAC | GGT | ATC | TAC | TTC | CGA | GAC | 840 |
|---|---|---|---|---|---|---|---|---|---|---|---|---|---|---|---|---|
| Asn | Ile | Thr | Tyr | Gly | Thr | Gly | Gly | Ala | Asn | Gly | Ile | Tyr | Phe | Arg | Asp | |
| | 80 | | | | | 85 | | | | | 90 | | | | | |

| AGC | ATT | ACT | GTC | GGC | GGT | GCT | ACC | GTG | AAG | CAG | CAA | ACT | TTG | GCT | TAC | 888 |
|---|---|---|---|---|---|---|---|---|---|---|---|---|---|---|---|---|
| Ser | Ile | Thr | Val | Gly | Gly | Ala | Thr | Val | Lys | Gln | Gln | Thr | Leu | Ala | Tyr | |
| 95 | | | | 100 | | | | | 105 | | | | | 110 | | |

| GTC | GAC | AAC | GTC | AGC | GGC | CCA | ACT | GCT | GAG | CAG | TCT | CCC | GAC | TCT | GAA | 936 |
|---|---|---|---|---|---|---|---|---|---|---|---|---|---|---|---|---|
| Val | Asp | Asn | Val | Ser | Gly | Pro | Thr | Ala | Glu | Gln | Ser | Pro | Asp | Ser | Glu | |
| | | | | 115 | | | | | 120 | | | | | 125 | | |

| CTC | TTC | CTT | GAT | GGT | ATC | TTC | GGC | GCA | GCC | TAC | CCT | GAC | AAC | ACT | GCC | 984 |
|---|---|---|---|---|---|---|---|---|---|---|---|---|---|---|---|---|
| Leu | Phe | Leu | Asp | Gly | Ile | Phe | Gly | Ala | Ala | Tyr | Pro | Asp | Asn | Thr | Ala | |
| | | | 130 | | | | | 135 | | | | | 140 | | | |

| ATG | GAA | GCC | GAA | TAC | GGA | GAT | ACT | TAC | AAC | ACT | GTC | CAC | GTT | AAC | CTC | 1032 |
|---|---|---|---|---|---|---|---|---|---|---|---|---|---|---|---|---|
| Met | Glu | Ala | Glu | Tyr | Gly | Asp | Thr | Tyr | Asn | Thr | Val | His | Val | Asn | Leu | |
| | | 145 | | | | | 150 | | | | | 155 | | | | |

| TAC | AAG | CAG | GGC | TTG | ATC | TCT | TCT | CCT | GTC | TTC | TCT | GTG | TAC | ATG | AAC | 1080 |
|---|---|---|---|---|---|---|---|---|---|---|---|---|---|---|---|---|
| Tyr | Lys | Gln | Gly | Leu | Ile | Ser | Ser | Pro | Val | Phe | Ser | Val | Tyr | Met | Asn | |
| | 160 | | | | | 165 | | | | | 170 | | | | | |

| ACC | AAC | GAC | GGT | GGC | GGC | CAA | GTT | GTC | TTT | GGT | GGC | GTC | AAC | AAC | ACC | 1128 |
|---|---|---|---|---|---|---|---|---|---|---|---|---|---|---|---|---|
| Thr | Asn | Asp | Gly | Gly | Gly | Gln | Val | Val | Phe | Gly | Gly | Val | Asn | Asn | Thr | |
| 175 | | | | | 180 | | | | | 185 | | | | | 190 | |

| CTT | CTC | GGA | GGA | GAC | ATT | CAA | TAC | ACT | GAC | GTT | TTG | AAG | AGC | CGA | GGC | 1176 |
|---|---|---|---|---|---|---|---|---|---|---|---|---|---|---|---|---|
| Leu | Leu | Gly | Gly | Asp | Ile | Gln | Tyr | Thr | Asp | Val | Leu | Lys | Ser | Arg | Gly | |
| | | | | 195 | | | | | 200 | | | | | 205 | | |

| GGC | TAC | TTC | TTC | TGG | GAT | GCC | CCT | GTC | ACC | GGT | GTC | AAA | ATT | GAT | GGA | 1224 |
|---|---|---|---|---|---|---|---|---|---|---|---|---|---|---|---|---|
| Gly | Tyr | Phe | Phe | Trp | Asp | Ala | Pro | Val | Thr | Gly | Val | Lys | Ile | Asp | Gly | |
| | | | 210 | | | | | 215 | | | | | 220 | | | |

| TCT | GAC | GCT | GTC | AGC | TTC | GAC | GGC | GCC | CAG | GCA | TTC | ACC | ATC | GAT | ACC | 1272 |
|---|---|---|---|---|---|---|---|---|---|---|---|---|---|---|---|---|
| Ser | Asp | Ala | Val | Ser | Phe | Asp | Gly | Ala | Gln | Ala | Phe | Thr | Ile | Asp | Thr | |
| | | | 225 | | | | | 230 | | | | | 235 | | | |

| | | | | | | | | | | | | | | | |
|---|---|---|---|---|---|---|---|---|---|---|---|---|---|---|---|
|GGC|ACC|AAC|TTC|TTC|ATC|GCA|CCC|TCC|AGC|TTT|GCC|GAG|AAG|GTT|GTA|1320|
|Gly|Thr|Asn|Phe|Phe|Ile|Ala|Pro|Ser|Ser|Phe|Ala|Glu|Lys|Val|Val| |
| |240| | | |245| | | | |250| | | | | | |

```
GGC ACC AAC TTC TTC ATC GCA CCC TCC AGC TTT GCC GAG AAG GTT GTA    1320
Gly Thr Asn Phe Phe Ile Ala Pro Ser Ser Phe Ala Glu Lys Val Val
    240             245                 250

AAG GCT GCA CTC CCC GAT GCT ACC GAG TCG CAG CAG GGT TAT ACT GTT    1368
Lys Ala Ala Leu Pro Asp Ala Thr Glu Ser Gln Gln Gly Tyr Thr Val
255             260                 265                     270

CCT TGC TCC AAG TAC CAG GAT TCC AAG ACC ACC TTC AGC CTT GTT CTG    1416
Pro Cys Ser Lys Tyr Gln Asp Ser Lys Thr Thr Phe Ser Leu Val Leu
            275                 280                 285

CAA AAG TCT GGT TCC AGC AGC GAT ACC ATT GAC GTC TCG GTT CCT ATT    1464
Gln Lys Ser Gly Ser Ser Ser Asp Thr Ile Asp Val Ser Val Pro Ile
            290                 295                 300

AGC AAG ATG CTT CTT CCA GTC GAT AAG TCG GGC GAG ACT TGC ATG TTC    1512
Ser Lys Met Leu Leu Pro Val Asp Lys Ser Gly Glu Thr Cys Met Phe
        305                 310                 315

ATC GTA CTT CCC GAT GGC GGT AAC CAG TTC ATT GTT GGC AAC CTC TTC    1560
Ile Val Leu Pro Asp Gly Gly Asn Gln Phe Ile Val Gly Asn Leu Phe
        320                 325                 330

TTG CGC TTC TTC GTC AAC GTT TAC GAC TTT GGC AAG AAC CGT ATC GGC    1608
Leu Arg Phe Phe Val Asn Val Tyr Asp Phe Gly Lys Asn Arg Ile Gly
335             340                 345                     350

TTT GCA CCT TTG GCT TCC GGA TAC GAG AAC AAC TAAAGGAATA CTCCCTGTTC  1661
Phe Ala Pro Leu Ala Ser Gly Tyr Glu Asn Asn
                355                 360

CCGACTTATC TACGTGTTAC GGTACTGTAT CTCTATCTTT ACTTTTAAC TGTATTCAAT   1721

AAATTATCTT GTTGTACTTT TACATGACTT TTGCGCTTGG TTAGCTCTTT GAAAGCATCA  1781

ATGTCACATT TTTTTCTCAG ACAACGAGGC ACTTTTGCAC TTTAGTCTGC CCGTATGCAA  1841

GTCGCAAAAG CAGCTTGACC TAGCTGACGG TATCATCCGT CAAGGATAAA AAGATCGCAA  1901

CTTAGTAGAC AATTCTGAAA CATTTCAACA ATGAGCAAAC AAACTTTGTT GGACGCATAT  1961

ATAACTCTGC CAAATATGAG ATAATATATT CAAATGAACT CTCAAGTT              2009
```

( 2 ) INFORMATION FOR SEQ ID NO:2:

( i ) SEQUENCE CHARACTERISTICS:
        ( A ) LENGTH: 427 amino acids
        ( B ) TYPE: amino acid
        ( D ) TOPOLOGY: linear ( i i ) MOLECULE TYPE: Protein ( i i i ) HYPOTHETICAL: NO ( x i ) SEQUENCE DESCRIPTION: SEQ ID NO:2:

```
Met Leu Phe Ser Lys Ile Ser Ala Ile Leu Leu Thr Ala Ala Ser
    -65             -60                 -55

Phe Ala Leu Thr Ser Ala Arg Pro Val Ser Lys Gln Ser Asp Ala Asp
-50             -45                 -40                     -35

Asp Lys Leu Leu Ala Leu Pro Leu Thr Ser Val Asn Arg Lys Tyr Ser
            -30                 -25                 -20

Gln Thr Lys His Gly Gln Gln Ala Ala Glu Lys Leu Gly Gly Ile Lys
            -15                 -10                 -5

Ala Phe Ala Glu Gly Asp Gly Ser Val Asp Thr Pro Gly Leu Tyr Asp
    1               5                   10

Phe Asp Leu Glu Glu Tyr Ala Ile Pro Val Ser Ile Gly Thr Pro Gly
15              20                  25                      30

Gln Asp Phe Tyr Leu Leu Phe Asp Thr Gly Ser Ser Asp Thr Trp Val
                35                  40                  45

Pro His Lys Gly Cys Asp Asn Ser Glu Gly Cys Val Gly Lys Arg Phe
            50                  55                  60
```

```
Phe Asp Pro Ser Ser Ser Ser Thr Phe Lys Glu Thr Asp Tyr Asn Leu
        65              70                  75

Asn Ile Thr Tyr Gly Thr Gly Gly Ala Asn Gly Ile Tyr Phe Arg Asp
        80              85                  90

Ser Ile Thr Val Gly Gly Ala Thr Val Lys Gln Gln Thr Leu Ala Tyr
 95             100             105                         110

Val Asp Asn Val Ser Gly Pro Thr Ala Glu Gln Ser Pro Asp Ser Glu
                115             120                 125

Leu Phe Leu Asp Gly Ile Phe Gly Ala Ala Tyr Pro Asp Asn Thr Ala
            130             135                 140

Met Glu Ala Glu Tyr Gly Asp Thr Tyr Asn Thr Val His Val Asn Leu
            145             150                 155

Tyr Lys Gln Gly Leu Ile Ser Ser Pro Val Phe Ser Val Tyr Met Asn
 160            165                 170

Thr Asn Asp Gly Gly Gly Gln Val Val Phe Gly Gly Val Asn Asn Thr
175             180             185                         190

Leu Leu Gly Gly Asp Ile Gln Tyr Thr Asp Val Leu Lys Ser Arg Gly
            195             200                 205

Gly Tyr Phe Phe Trp Asp Ala Pro Val Thr Gly Val Lys Ile Asp Gly
            210             215                 220

Ser Asp Ala Val Ser Phe Asp Gly Ala Gln Ala Phe Thr Ile Asp Thr
        225             230                 235

Gly Thr Asn Phe Phe Ile Ala Pro Ser Ser Phe Ala Glu Lys Val Val
240             245                 250

Lys Ala Ala Leu Pro Asp Ala Thr Glu Ser Gln Gln Gly Tyr Thr Val
255             260                 265                     270

Pro Cys Ser Lys Tyr Gln Asp Ser Lys Thr Thr Phe Ser Leu Val Leu
            275             280                     285

Gln Lys Ser Gly Ser Ser Ser Asp Thr Ile Asp Val Ser Val Pro Ile
            290             295                 300

Ser Lys Met Leu Leu Pro Val Asp Lys Ser Gly Glu Thr Cys Met Phe
        305             310                 315

Ile Val Leu Pro Asp Gly Gly Asn Gln Phe Ile Val Gly Asn Leu Phe
        320             325                 330

Leu Arg Phe Phe Val Asn Val Tyr Asp Phe Gly Lys Asn Arg Ile Gly
335             340                 345                     350

Phe Ala Pro Leu Ala Ser Gly Tyr Glu Asn Asn
            355             360
```

( 2 ) INFORMATION FOR SEQ ID NO:3:

( i ) SEQUENCE CHARACTERISTICS:
        ( A ) LENGTH: 20 bases
        ( B ) TYPE: nucleic acid
        ( C ) STRANDEDNESS: single
        ( D ) TOPOLOGY: linear ( i i ) MOLECULE TYPE: Other nucleic acid, synthetic DNA ( i i i ) HYPOTHETICAL: NO ( i v ) ANTI-SENSE: NO ( x i ) SEQUENCE DESCRIPTION: SEQ ID NO:3:

GTCTTTGGTN NCGTCAACCA                     20

( 2 ) INFORMATION FOR SEQ ID NO:4:

( i ) SEQUENCE CHARACTERISTICS:
        ( A ) LENGTH: 81 bases (B) TYPE: nucleic acid
        (C) STRANDEDNESS: single
        (D) TOPOLOGY: linear (ii) MOLECULE TYPE: Other nucleic acid, recombinant DNA (iii) HYPOTHETICAL: NO (iv) ANTI-SENSE: NO (ix) FEATURE:
        (A) NAME/KEY: CDS
        (B) LOCATION: 67 to 81

(xi) SEQUENCE DESCRIPTION: SEQ ID NO:4:

ATAAAAAAAA CAGTTGAATA TTCCCTCAAA AAGGGGATCA CTCTGAGACC TCATCAAATC    60

CTCAAC ATG CTC TTC TCC AAG    81
       Met Leu Phe Ser Lys
                         5

(2) INFORMATION FOR SEQ ID NO:5:

(i) SEQUENCE CHARACTERISTICS:
        (A) LENGTH: 5 amino acids
        (B) TYPE: amino acid
        (D) TOPOLOGY: linear (ii) MOLECULE TYPE: Protein (iii) HYPOTHETICAL: NO (xi) SEQUENCE DESCRIPTION: SEQ ID NO:5:

Met Leu Phe Ser Lys
                 5